(12) United States Patent
Mellon

(10) Patent No.: US 9,597,336 B2
(45) Date of Patent: Mar. 21, 2017

(54) THERAPY FOR TREATMENT OF CHRONIC DEGENERATIVE BRAIN DISEASES AND NERVOUS SYSTEM INJURY

(71) Applicant: THE REGENTS OF THE UNIVERSITY OF CALIFORNIA, Oakland, CA (US)

(72) Inventor: Synthia Mellon, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/062,598

(22) Filed: Oct. 24, 2013

(65) Prior Publication Data

US 2014/0148427 A1 May 29, 2014

Related U.S. Application Data

(63) Continuation of application No. 11/576,125, filed as application No. PCT/US2005/034746 on Sep. 27, 2005, now Pat. No. 8,604,011.

(60) Provisional application No. 60/613,880, filed on Sep. 27, 2004.

(51) Int. Cl.
*A61K 31/56* (2006.01)
*A61K 31/57* (2006.01)

(52) U.S. Cl.
CPC .................................. *A61K 31/57* (2013.01)

(58) Field of Classification Search
CPC ....................................................... A61K 31/57
USPC ........................................................ 514/182
See application file for complete search history.

(56) References Cited

U.S. PATENT DOCUMENTS

2002/0072509 A1* 6/2002 Stein et al. .................. 514/169
2005/0003998 A1   1/2005 Bertilsson et al.

OTHER PUBLICATIONS

Neufeld (Annu. Rev. Biochem. 1991, 60, 257-80).*
Bramlett, K. S. et al., "A Natural Product Ligand of the Oxysterol Receptor, Liver X Receptor", *The Journal of Pharmacology and Experimental Therapeutics*, vol. 307, pp. 291-296 (2003).
Burns and Duff, "Brain on steroids resists neurodegeneration", *Nature Medicine*, vol. 10, No. 7, pp. 675-676 (2004).
Collins, Jon L., "Therapeutic opportunities for liver X receptor modulators", *Current Opinion in Drug Discovery & Development*, vol. 7, No. 5, pp. 692-702 (2004).
Frolov, A. et al., "NPC1 and NPC2 Regulate Cellular Cholesterol Homeostasis through Generation of Low Density Lipoprotein Cholesterol-derived Oxysterols", *The Journal of Biological Chemistry*, vol. 278, No. 28, pp. 25517-25525 (2003).
Griffin, Lisa D. et al., "Niemann-Pick type C disease involves disrupted neurosteroidogenesis and responds to allopregnanolone", *Nature Medicine*, vol. 10, No. 7, pp. 704-711 (2004).
Mellon, S. et al., "Endogenous and synthetic neurosteroids in treatment of Niemann-Pick Type C disease", *Brain Research Reviews*, vol. 57, pp. 410-420 (2008).
di Michelle, F. et al., "Decreased plasma and cerebrospinal fluid content of neuroactive steroids in Parkinson's disease", *Neurol. Sci.* vol. 24, pp. 172-173 (2003).
NINDS, NIH Document, http://www.ninds.nih.gov/disorders/neimann.htm), p. 1-2 (2010).
Reddy, D. S., "Pharmacology of Endogenous Neuroactive Steroids", *Critical Reviews in Nerobiology*, vol. 15, No. 3&4, pp. 197-234 (2003).
Rupprecht, R., "Neuroactive steroids: mechanisms of action and neuropsychopharmacological properties", *Psychoneuroendocrinology*, vol. 28, pp. 139-168 (2003).
Timby, E. et al., "Alloprenanolone, a $GABA_A$ receptor agonist, decreases gonadotropin levels in women. A preliminary study." *Gynecological Endocrinology*, pp. 1-7 (2010).
Weill-Engerer, S. et al., "Neurosteroid Quantification in Human Brain Regions: Comparison between Alzheimer's and Nondemented Patients", *The Journal of Clinical Endocrinology*, vol. 87, No. 11, pp. 5138-5143 (2002).

* cited by examiner

*Primary Examiner* — Uma Ramachandran
(74) *Attorney, Agent, or Firm* — Morgan, Lewis & Bockius LLP; Jeffry S. Mann

(57) ABSTRACT

In one aspect, the present invention provides neuroactive steroids for use in the treatment of nervous system disorders, degenerative brain diseases and congenital storage diseases. In a second aspect, the invention provides neuroactive steroids in combination with a Liver X Receptor (LXR) ligand to effect treatment of a nervous system condition.

3 Claims, 8 Drawing Sheets

THERAPY FOR TREATMENT OF CHRONIC DEGENERATIVE BRAIN DISEASES AND NERVOUS SYSTEM INJURY

RELATED APPLICATIONS

This application is a continuation of U.S. application Ser. No. 11/576,125 filed May 13, 2008, which is a U.S. National Stage under 35 USC 371 of PCT/US2005/034746 filed Sep. 27, 2005, which claims priority to U.S. Provisional Patent Application No. 60/613,880 filed Sep. 27, 2004, the contents of each of which are incorporated herein by reference in their entirety for all purposes.

STATEMENT AS TO RIGHTS TO INVENTIONS MADE UNDER FEDERALLY SPONSORED RESEARCH OR DEVELOPMENT

This invention was made with Government support under Grant No. HD27970 awarded by the National Institutes of Health. The Government has certain rights in this invention.

BACKGROUND OF THE INVENTION

Field of the Invention

The present invention relates to methods of providing therapy for nervous system conditions including, but not limited to: degenerative brain diseases, ganglioside storage disorders and inflammatory disorders.

Background

There are more than 600 known disorders that afflict the nervous system. Nervous system disorders have varied etiologies, but ultimately all have devastating effects on the individuals suffering from them. Nervous system disorders include degenerative conditions such as Parkinson's and Alzheimer's disease; inflammatory diseases such as Multiple sclerosis, spinal cord injury ischemia and stroke, psychiatric disorders such as schizophrenia, and lipid storage disorders such as Neimann-Pick-C, Tay Sachs, Batten, Sandhoff and Gaucher disease.

Neurological disorders strike an estimated 50 million Americans each year, exacting an incalculable personal toll and an annual economic cost of hundreds of billions of dollars in medical expenses and lost productivity.

The burden of neurological disease is a burden borne by every segment of society, and people everywhere. Indeed, individuals suffering from nervous system disorders often a require care 24 hours a day, seven days a week. In such cases family members from several households may need to partake in the care, and these caregivers usually have jobs, as well as their own families. Thus, the consequences of neurological disease have far reaching consequences.

Neurological disorders may be manifest at any stage of life. Some neurological diseases typically exhibit adult onset. These include Alzheimer's Disease, Amyotrophic Lateral Sclerosis, Huntington's Disease, Multiple Sclerosis, Parkinson's Disease, Stroke, and traumatic brain injury. Adult onset neurological disease accounts for between 13.3 and 16.1 million cases of neurological disorders in the United States. Unfortunately, many of these diseases and disorders are progressive, so that the burden of care for the individual increases with time.

Other neurological diseases affect infants and children. Indeed, glycosphingolipid storage diseases are a common cause of pediatric neurodegenerative diseases. Although the frequency of individual disorders is not high, together they are a significant group of disorders with a collective frequency of 1 in 18,000 live births.

Unfortunately, neurologic disease is seldom curable. This is true irrespective of the age at which the neurological disease is manifest. Thus, strategies for the treatment of these debilitating and often fatal diseases often focus primarily on palliative measures. Attempts at curing neurological disease have also been proposed. These treatments have included enzyme replacement therapy, gene therapy, and allogenic bone marrow transplantation. Unfortunately however, the treatments typically do not improve the condition nor alter the ultimate outcome of the disease. Thus, before this invention, symptomatic management was often the only approach available for treating most of these disorders.

The present inventors have determined for the first time that the use of neuroactive steroids is effective for the treatment of degenerative brain diseases and central nervous system disorders.

Managing the neuropathologic processes that contribute to the morbidity of neurologic diseases has proven to be a challenging task, since as noted above, there are many factors that can cause, perpetuate, or exacerbate neurological conditions involving the central nervous system. There has been no evidence prior to this invention that neuroactive steroids would provide effective therapy for the treatment of a wide range of neurological diseases, including congenital lipid storage diseases, inflammatory diseases, and chronic degenerative brain disease. The present invention therefore fulfills the need for an effective method of treating neurological disorders by providing methods of administering neuroactive steroids to a subject.

There is immunostaining for both MAC1 and MHC II in the thalamus of untreated NP-C mice, which is substantially reduced in day 7-allopregnanolone-treated NP-C mice. Wh=white matter.

Figure 5:
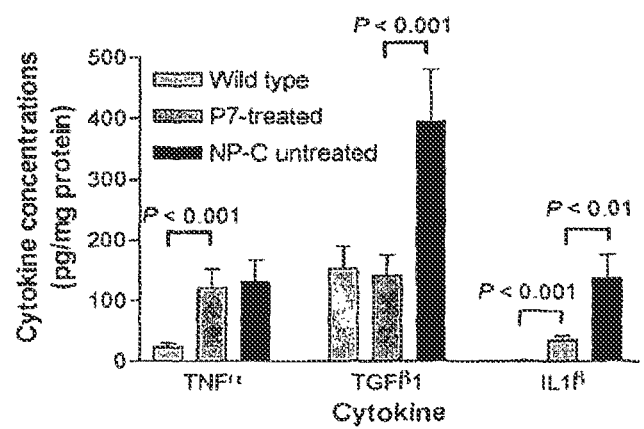

FIG. 5: Cytokine concentrations in Adult Wild type, Untreated NP-C and allopregnanolone-Treated (day 7) NP-C mice. The cytokines TGFβ and IL1β are substantially reduced in day 7-allopregnanolone-treated NP-C mice, in comparison to untreated NP-C mice.

Figure 6:
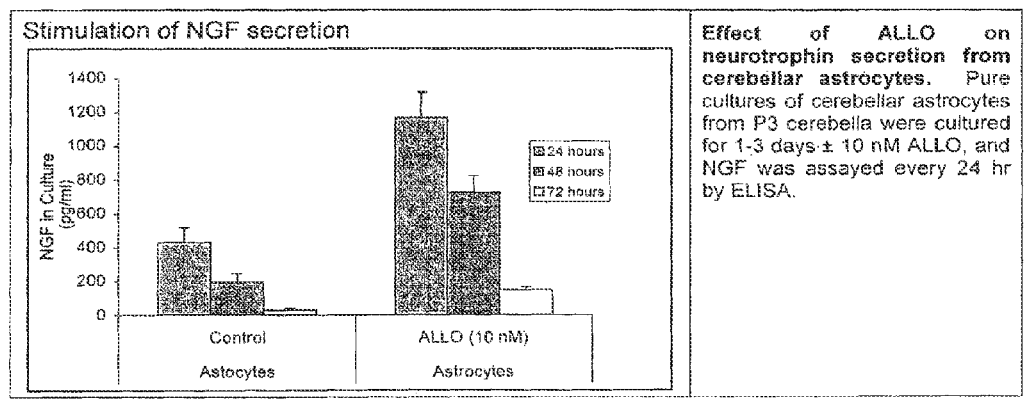

FIG. 6: Allopregnanolone stimulation of neurotrophin secretion in cultured cells.

Figure 7:
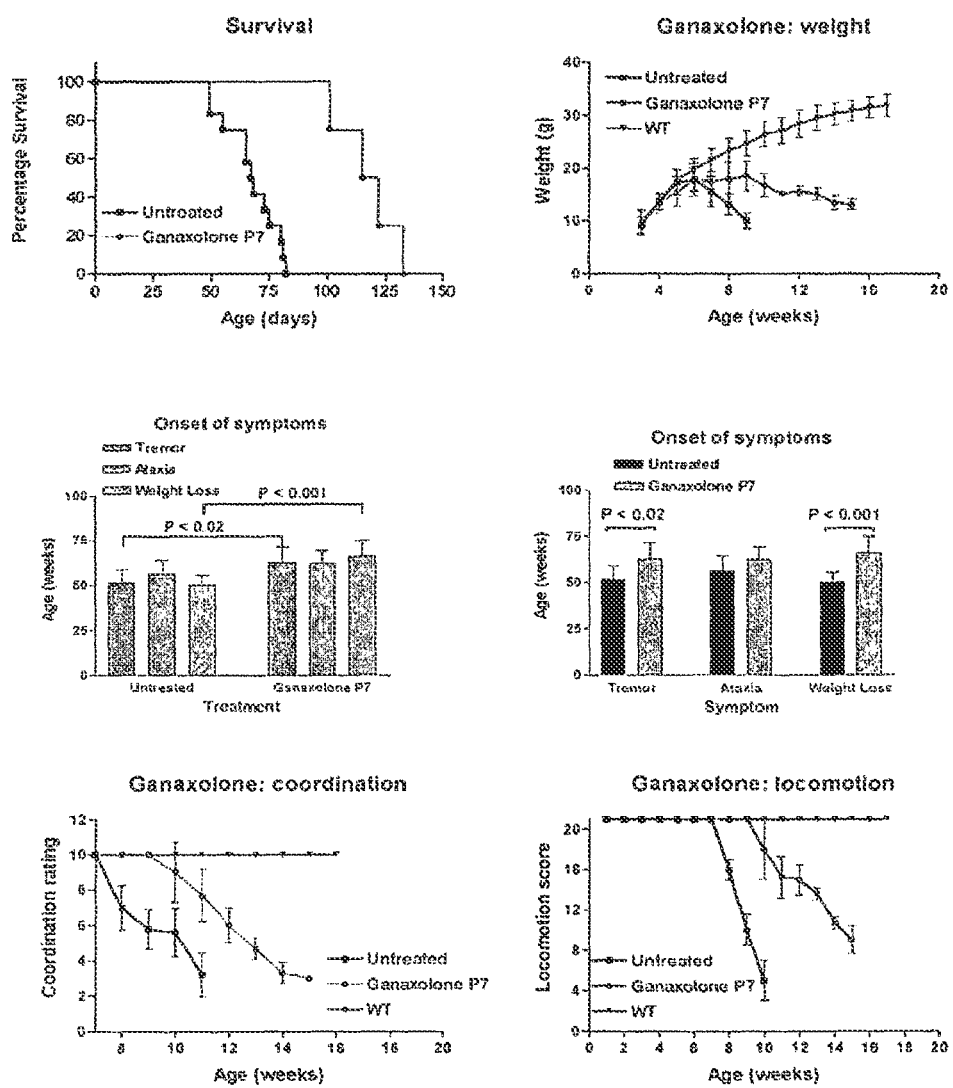

FIG. 7: Effect of ganaxolone on progression of NP-C symptoms: Ganaxolone (25 mg/kg in 20% β-cyclodextrin) was administered subcutaneously in a single injection at P7 (n=12 mice for untreated and wild type; n=4 mice for ganaxolone treatment).

Figure 8:
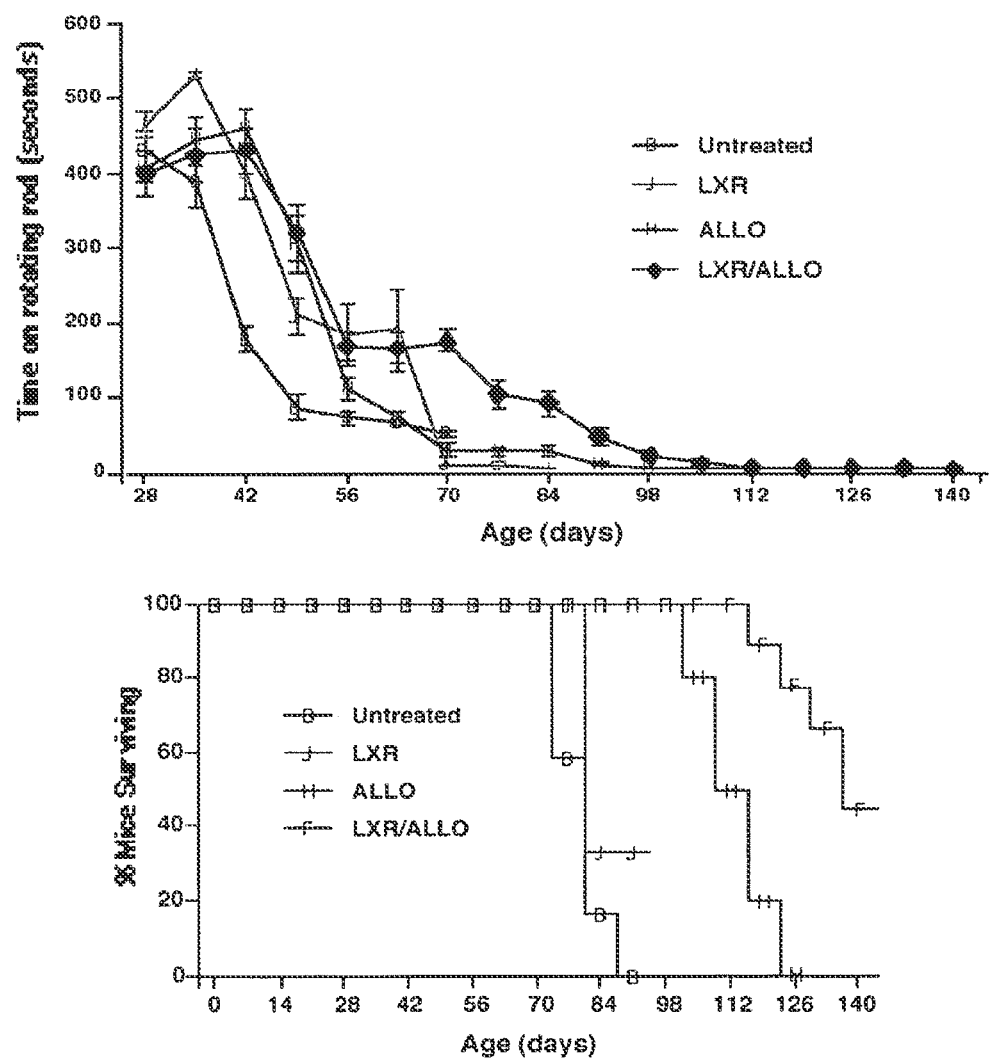

FIG. 8: Effect of an LXR ligand T0901317, Allopregnanolone, and a combination of both T0901317 plus allopregnanolone on progression of NP-C symptoms. T0901317 was given at 50 mg/kg/day beginning at P (postnatal day) 18. Allopregnanolone (25 mg/kg in 20% β-cyclodextrin) was administered subcutaneously in a single injection at P (postnatal day) 7 (n=12 mice for each treatment). LXR ligand or Allopregnanolone treatment delayed the onset of symptoms, and LXR ligand blunted the decline in symptoms. The combination therapy delayed the onset of symptoms and decline in neurologic function, assessed by rotorod trials. The combination therapy also significantly prolonged the lifepan of the NP-C mice (mean 136 days) compared with allopregnanolone treatment alone (mean 112 days) or LXR ligand alone (mean 80 days), vs. untreated NP-C mouse (mean 74 days).

SUMMARY OF THE INVENTION

The use of neuroactive steroids in the treatment of central nervous system disorders and degenerative brain diseases has not been described previously. However, it has now been discovered that a variety of neurological disorders, including, but not limited to congenital storage diseases, may benefit from treatments with neuroactive steroids. Thus, in one aspect, the invention provides a method to effect treatment of a nervous system condition. The method comprises administering to a patient in need thereof, an effective amount of a composition comprising a compound having a structure according to Formula (I):

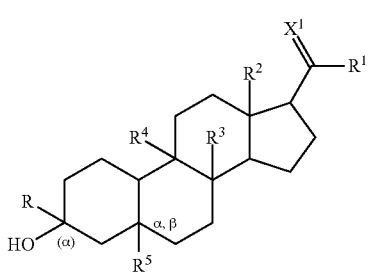

(I)

wherein R is a member selected from H, substituted or unsubstituted alkyl, substituted or unsubstituted heteroalkyl and substituted or unsubstituted aryl; and X1 is a member selected from O, S and NR6. R6 is a member selected from H, OR7, substituted or unsubstituted alkyl, substituted or unsubstituted heteroalkyl and substituted or unsubstituted aryl. R7 is a member selected from H, substituted or unsubstituted alkyl, substituted or unsubstituted heteroalkyl and substituted or unsubstituted aryl. R1 is a member selected from H, OR8, NR8R9, substituted or unsubstituted alkyl, substituted or unsubstituted heteroalkyl and substituted or unsubstituted aryl; and R8 is a member selected from H, C(X2)R10, substituted or unsubstituted alkyl, substituted or unsubstituted heteroalkyl and substituted or unsubstituted aryl. X2 is a member selected from O, S and NH; R10 is a member selected from substituted or unsubstituted alkyl, substituted or unsubstituted heteroalkyl and substituted or unsubstituted aryl; R9 is a member selected from H, substituted or unsubstituted alkyl and substituted or unsubstituted heteroalkyl; and R2, R3, R4 and R5 are members independently selected from H, substituted or unsubstituted alkyl, and substituted or unsubstituted heteroalkyl. In an exemplary embodiment, the nervous system condition is a lysosomal storage disorder.

In an exemplary embodiment, R is selected from substituted or unsubstituted alkyl. In another embodiment R is $CH_3$.

In other exemplary embodiments the invention provides a method for ameliorating the symptoms or signs of an inflammatory disorder, and/or nervous system conditions characterized by a change in the permeability of the blood brain barrier. In other embodiments, the invention provides therapy for the treatment of Multiple Sclerosis, Alzheimer's Disease, Parkinson's Disease, spinal cord injury, ischemia, and stroke.

In other exemplary embodiments the invention provides therapy for a lysosomal storage disorder. The lysosomal storage disorder is characterized by abnormalities of cholesterol metabolism. In an exemplary embodiment, the abnormality of cholesterol metabolism is further associated with a cardiovascular disorder. In an exemplary embodiment, the cardiovascular disorder is a member selected from heart disease and atherosclerosis. In an alternative embodiment, the lysosomal storage disorder is a sphingolipid storage disease. Exemplary sphingolipid storage diseases for which the invention provides effective therapy include, but are not limited to: GM1 and GM2 gangliosidosis, Tay Sachs Disease, Batten, Sandhoff, Gaucher disease, Fabry's disease, Niemann Pick A and B, Niemann Pick-C, Schindler Disease, Farber disease, Krabbe Disease, Austin Disease, Sulfatidosis, Fucosidosis, and mucopolysaccharidosis.

In another exemplary embodiment, the invention provides a method of therapy that ameliorates the signs and symptoms of a neurodegenerative disease. Neurodegenerative diseases for which the invention provides effective therapy include, but are not limited to Alzheimer's disease, Parkinson's disease, amyotrophic lateral sclerosis, and Huntington's disease.

In another exemplary embodiment, the invention provides effective therapy for the treatment of a demyelinating disorder which in exemplary instances is manifest as Multiple Sclerosis, optic neuritis, transverse neuritis and/or Guillain-Barre Syndrome.

In still another exemplary embodiment the invention provides a method for ameliorating the signs and symptoms of a leukodystrophy. The leukodystrophy may include metachromatic leukodystrophy, Krabbe disease, adrenoleukodystrophy, Pelizaeus-Merzbacher disease, Canavan disease, Childhood Ataxia with Central Hypomyelination or CACH (also known as Vanishing White Matter Disease), Alexander disease, Refsum disease, and cerebrotendinous xanthomatosis.

In another exemplary embodiment, the invention provides an effective treatment for neurological conditions involving disruptions of brain cellular metabolism. Exemplary conditions involving disruptions of brain cellular metabolism include, but are not limited to hypoglycemia, acidosis, hypoxia, or hypercarbia, which may be brought on by extracellular events. An exemplary extracellular event includes, but is not limited to, a disruption of extracellular fluid composition triggered by hypernatremia, hyponatremia, hyperosmolality, hypoosmolality, hypercalcemia, hypocalcemia, hypermagnesemia, hypomagnesemia, hyperphosphatemia, and/or hypophosphatemia.

In another exemplary embodiment, the invention provides effective therapy for a neurological condition that is a psychiatric condition. Exemplary psychiatric conditions include, but are not limited to, frontotemporal dementias, movement disorders, psychoses, schizophrenia, depression, alcoholism, premenstrual dysphoric disorder, posttraumatic stress disorder, and/or social isolation.

In another aspect the invention provides a combination therapy for treatment of a nervous system condition. The method comprises administering to a patient in need thereof, effective amounts of a compound according to Formula (I) described above and a Liver X Receptor (LXR) ligand.

In an exemplary embodiment, the LXR ligand is either an oxysterol or a non-oxysterol. Exemplary oxysterol LXR ligands include, but are not limited to, TO901317, 22(R)-hydroxycholesterol, 24(S)-hydroxycholesterol, 24(S),25-epoxycholesterol, and 27-hydroxycholesterol. Exemplary non-oxysterol LXR ligands include, but are not limited to, Paxilline.

In still another aspect, the invention provides a pharmaceutical composition comprising effective amounts of a compound according to Formula (I) described above, a LXR ligand, and a pharmaceutically acceptable carrier.

Additional aspects, advantages and objects of the present invention will be apparent from the detailed description that follows.

DETAILED DESCRIPTION OF THE INVENTION

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization are those well known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses. The symptomology and diagnositic criteria for medical and psychiatric conditions is also known in the art and can be found in such texts as DSM-IV-TR (American Psychiatric Association: *Diagnostic and Statistical Manual of Mental Disorders*, Fourth Edition, Text Revision, Washington D.C., American Psychiatric Association (2000); *The Merck Manual of Diagnosis and Therapy* 17th Edition (1999) and *The Patholoic Basis of Disease*, Vinay Kumar, Nelson Fausto, Abul K. Abbas eds. (2004).

The term "therapy" refers to "treating" or "treatment" of a disease including preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

The term "ameliorating" or "ameliorate" refers to any indicia of success in the treatment of a pathology or condition, including any objective or subjective parameter such as abatement, remission or diminishing of symptoms or an improvement in a patient's physical or mental well-being. Amelioration of symptoms can be based on objective or subjective parameters; including the results of a physical examination and/or a psychiatric evaluation.

The term "nervous system condition" refers to a disease or disorder involving the nervous system. The condition can be psychological, physical, or both physical and psychological.

The term "effective amount" or a "therapeutically effective amount" means the amount that, when administered to an animal for treating a disease, is sufficient to effect treatment for that disease.

As used herein, "administering" means oral administration, administration as a suppository, topical contact, intravenous, intraperitoneal, intramuscular, intralesional, or subcutaneous administration, administration by inhalation, or the implantation of a slow-release device, e.g., a mini-osmotic pump, to the subject. Administration is by any route including parenteral and transmucosal (e.g., oral, nasal, vaginal, rectal, or transdermal), particularly by inhalation. Parenteral administration includes, e.g., intravenous, intramuscular, intra-arteriole, intradermal, subcutaneous, intraperitoneal, intraventricular, and intracranial. Moreover, where injection is to treat a tumor, e.g., induce apoptosis, administration may be directly to the tumor and/or into tissues surrounding the tumor. Other modes of delivery include, but are not limited to, the use of liposomal formulations, intravenous infusion, transdermal patches, etc.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups, which are limited to hydrocarbon groups are termed "homoalkyl".

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N, S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, and —CH═CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") include both substituted and unsubstituted forms of the indicated radical. Preferred substituents for each type of radical are provided below.

Substituents for the alkyl, and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generally referred to as "alkyl substituents" and "heteroakyl substituents," respectively, and they can be one or more of a variety of groups selected from, but not limited to: —OR', ═O, ═NR', ═N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')═NR"", —NR—C(NR'R")═NR"', —S(O)R', —S(O)$_2$R', —S(O)$_2$NR'R", —NRSO$_2$R', —CN and —NO$_2$ in a number ranging from zero to (2 m'+1), where m' is the total number of carbon atoms in such radical. R', R", R"' and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R"' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, the aryl substituents and heteroaryl substituents are generally referred to as "aryl substituents" and "heteroaryl substituents," respectively and are varied and selected from, for example: halogen, —OR', ═O, ═NR', ═N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl. When a compound of the invention includes more than one R group, for example, each of the R groups is independently selected as are each R', R", R'" and R"" groups when more than one of these groups is present.

Two of the aryl substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$)alkyl.

The term "inflammatory disorder" refers to any deviation from baseline functioning of organismal physiology caused by, or related to, inflammation or inflammatory processes. "Inflammation" is a fundamental pathological process comprising a dynamic complex of cytological and chemical reactions that occur in the affected blood vessels and adjacent tissues in response to injury or abnormal stimulation. Inflammation may arise in response to stimulation or damage from any physical, chemical, or biological agent. The physical, chemical, or biological agent(s) may be endogenous or exogenous factors. An example of an exogenous factor includes, but is not limited to; physical trauma such as compression from a blow or strike, or biological factors such as infection. Examples of endogenous factors include, chemical imbalances such as those arising from disease, and biological factors, such as the biological responses that lead to repair and healing of injury. Inflammation may be acute or chronic. Typically, chronic inflammation involves the interaction of antigens, antibodies, and autoantigens.

The term "blood brain barrier" refers to a selective partition, regulating the exchange of substances, including peptides, between the central nervous system (CNS) and the peripheral circulation.

The endothelial cells of the brain capillaries, are more tightly joined to one another than are those of other capillaries. These endothelial tight junctions contribute to formation of the blood brain barrier, slowing the diffusion of water-soluble drugs, and preventing certain circulating compounds from reaching the brain. However, the tight junctions are not solely responsible for creating the blood brain barrier. The glial connective tissue cells (astrocytes), form an astrocytic sheath close to the basement membrane of the capillary endothelium also contribute to the formation and maintenance of the blood-brain barrier. Because the capillary wall rather than the parenchymal cell forms the barrier, the brain's permeability characteristics differ from those of other tissues.

The expression "a change in the permeability of the blood brain barrier" refers to any deviation from the normal permeability characteristics associated with the blood-brain barrier.

The term "Multiple Sclerosis" refers to an acquired slowly progressive central nervous system disease characterized by disseminated patches of demyelination in the brain and spinal cord, resulting in multiple and varied neurologic symptoms and signs, usually with remissions and exacerbations. The disease is both an inflammatory disorder and a demyelinating disorder. Common presenting symptoms include paresthesias in one or more extremities, in the trunk, or on one side of the face; weakness or clumsiness of a leg or hand; visual disturbances, e.g., partial blindness and pain in one eye (retrobulbar optic neuritis), dimness of vision, or scotomas. Other common early symptoms are ocular palsy resulting in double vision (diplopia), transient weakness of one or more extremities, slight stiffness or unusual fatigability of a limb, minor gait disturbances, difficulty with bladder control, vertigo, and mild emotional disturbances; all indicating scattered CNS involvement and often occurring months or years before the disease is recognized. Excess heat (e.g., warm weather, a hot bath, a fever) may accentuate symptoms and signs.

The course of the disease is highly varied, unpredictable, and, in most patients, remittent. Life span is probably not shortened except in the most severe cases. At first, months or years of remission may separate episodes, especially when the disease begins with retrobulbar optic neuritis. Remissions can last >10 yr. However, some patients have frequent attacks and are rapidly incapacitated. Further elaboration of the symptomology of Multiple Sclerosis as well as diagnostic criteria, may be found in e.g., The Merck Manual of Diagnosis and Therapy, supra.

The term "Alzheimer's Disease" refers to a progressive, inexorable loss of cognitive function characterized by the appearance of two distinct abnormal proteinaceous deposits in regions of the brain responsible for learning and memory (e.g., cerebral cortex and hippocampus). These deposits are extracellular amyloid plaques, and intracellular neurofibrillary tangles (NFTs) comprising tau protein.

Alzheimer's disease often displays distinct clinical stages. However, patients vary greatly, and disease progression often is not as orderly as the following description implies. Typically the disease progresses gradually, although sometimes symptoms seem to plateau for a time. The early stage is characterized by loss of recent memory, inability to learn and retain new information, language problems, mood swings, and personality changes. Patients may have progressive difficulty performing activities of daily living. Abstract thinking or proper judgment may be diminished. Patients may respond to loss of control and memory with irritability, hostility, and agitation, and onset of emotional lability. In the intermediate stage, patients are unable to learn and recall new information. Memory of remote events is affected but not totally lost. Patients may require assistance with bathing, eating, dressing, or toileting. Behavioral disorganization may be characterized by wandering, agitation, hostility, uncooperativeness, or physical aggressiveness. By this stage, patients lose all sense of time and place and often get lost, sometimes to the point of being unable to find their own bedroom or bathroom. Although they remain ambulatory, they are at risk for falls or accidents secondary to confusion. In the severe stage, patients are unable to walk or to perform any activity of daily living and usually are totally incontinent. Recent and remote memory is completely lost. Patients may be unable to swallow and eat and are at risk of malnutrition, pneumonia, and pressure sores. Eventually, patients become mute. Because such patients cannot relate any symptoms to the physician and because elderly patients often have no febrile or leukocytic response to infection, the physician must rely on experience and acumen whenever a patient looks ill. Motor or other focal neurologic features occur very late in the disease, although the incidence of seizures is somewhat increased at all stages. The end stage of Alzheimer's disease is coma and death, usually from infection. Further the symptomology of Alzheimer's disease as well as diagnostic criteria, may be found in e.g., The Merck Manual of Diagnosis and Therapy, supra.

The term "Parkinson's Disease" refers to an idiopathic, slowly progressive, degenerative CNS disorder characterized by slow and decreased movement, muscular rigidity, resting tremor, and postural instability. Early signs include infrequent blinking and lack of facial expression, decreased movement, impaired postural reflexes, and the characteristic gait abnormality, suggest the disease. Tremor occurs initially in about 70% of patients but often becomes less prominent as the disease progresses. Although rigidity is occasionally minimal or lacking, tremor without the above features suggests an alternate diagnosis or the need for a later reevaluation, because additional signs will develop if the patient has Parkinson's disease.

The term "spinal cord injury" refers to a condition occurring when a traumatic event results in damage to cells within the spinal cord, or when the nerve tracts that relay signals up and down the spinal cord are severed. Some of the most common types of spinal cord injury include contusion and compression. Other types of injuries include, but are not limited to lacerations, and central cord syndrome. Severe spinal cord injury often causes paralysis and loss of sensation and reflex function below the point of injury, including autonomic activity such as breathing and other activities such as bowel and bladder control. Other symptoms such as pain or sensitivity to stimuli, muscle spasms, and sexual dysfunction may develop over time. Spinal cord injury patients are also prone to develop secondary medical problems, such as bladder infections, lung infections, and bed sores.

The term "ischemia" refers to local anemia due to mechanical obstruction of the blood supply. Myocardial ischemia is typically associated with coronary artery disease.

The term "stroke" refers to a condition wherein the blood flow to the brain stops. The most common type of stroke is an ischemic stroke, which may be caused by a blood clot that blocks a blood vessel or artery in the brain. Another, less common, type of stroke is a hemorrhagic stroke, which may be caused when a blood vessel in the brain ruptures and spills blood into the surrounding tissue. The symptoms of stroke happen immediately and include, but are not limited to numbness or weakness in the face, arms, or legs; confusion, difficulty speaking or understanding speech; vision disturbances in one or both eyes; dizziness, trouble walking, loss of balance or coordination; and severe headache with no known cause. "Stroke" (i.e., cerebrovascular disease) is the third leading cause of death in the developed world, and an extremely important cause of disability.

The term "abnormalities of cholesterol metabolism" refers to any deviation from the baseline, homeostatic functioning of those metabolic pathways involved in cholesterol metabolism.

The term "cardiovascular disorder" refers to any disorder relating to the heart, blood vessels or circulation.

The term "heart disease" refers to a heart condition that typically is associated with coronary disease. Coronary disease develops when one or more arteries that supply blood to the heart become narrowed or clogged as a result of atherosclerosis.

The term "atherosclerosis" refers to the build up of deposits of fatty substances, cholesterol, cellular waste products, calcium and other substances in the inner lining of an artery. The buildup is called plaque. Plaques can grow large enough to significantly reduce the blood's flow through an artery. However, most of the damage occurs when plaques become fragile and rupture. Plaques that rupture cause blood clots to form that can block blood flow or break off and travel to another part of the body. If either happens and blocks a blood vessel that feeds the heart, it may cause a heart attack. If it blocks a blood vessel that feeds the brain, it may cause a stroke. And if blood supply to the arms or legs is reduced, it can cause difficulty walking, and may eventually cause gangrene.

The terms "lysosomal storage disorder" or "lipid storage disorder" refer to a family of diverse diseases related by molecular pathology. In each disorder, a deficiency of a lysosomal hydrolase is inherited, which leads to lysosomal accumulation of the enzyme's specific sphingolipid substrate. Disorders include GM1 gangliosidoses, GM2 gangliosidoses, Gaucher disease, Niemann-Pick disease, Fabry disease, fucosidosis, Schindler disease, metachromatic leukodystrophy, Krabbe disease, multiple sulfatase deficiency, Farber disease, and Wolman disease. The biochemical basis of lipid storage disorders is well characterized. Diagnostic assays for identification of affected individuals are available and are known to those of skill in the art. (see e.g., The Merck Manual of Diagnostics and Therapy, supra). Diagnostic assays typically employ the measurement of specific enzymatic activity in isolated leukocytes or cultured fibroblasts. The diseases may lead to neurodegenerative disease, organomegaly, skeletal abnormalities, pulmonary infiltration, and other manifestations.

The term "sphingolipid storage disease" refers to a condition wherein endogenous lipids accumulate in the lysosomes of many different cell types in the body. In some cases the disorder may be associated with defective breakdown of sphingolipids, resulting in different diseases depending of which step of the degradation pathways is affected. For example, in some lipid storage diseases, such as Niemann Pick Type-C(NP-C) and Mucolipidosis Type IV (ML-IV) lipid accumulation in the lysosomes results from defects in transport to or from the lysosomes rather than defects in the degradative pathways.

The term "GM1 gangliosodosis" refers to a disorder of infants in which the ganglioside $GM_1$ accumulates in the nervous system. The patient often dies by age 2.

The term "GM2 gangliosodosis" or "Tay Sachs Disease" refers to a condition characterized by very early onset, progressive retardation in development, paralysis, dementia, blindness, cherry-red retinal spots, and death by age 3 or 4. This autosomal recessive disorder is most common in Jewish families of Eastern European origin. The condition is associated with a deficiency of the enzyme hexosaminidase A, resulting in accumulation of gangliosides (complex sphingolipids) in the brain.

The term "Sandhoff Disease" refers to a rare, genetic, lipid storage disorder resulting in the progressive deterioration of the central nervous system. Like Tay Sachs Disease (above) "Sandhoff Disease" is associated with a deficiency of the enzyme hexosaminidase which results in the accumulation of certain fats (lipids) in the brain and other organs of the body. Although Sandhoff disease may be considered severe form of Tay-Sachs disease it is not limited to any ethnic group. Onset of the disorder usually occurs at 6 months of age. Symptoms may include motor weakness, startle reaction to sound, early blindness, progressive mental and motor deterioration, frequent respiratory infections, macrocephaly, doll-like facial appearance, cherry-red spots in the back of the eyes, seizures, and myoclonus. The prognosis for individuals with Sandhoff disease is poor. Death usually occurs by age 3 and is generally caused by respiratory infections.

The term "Batten Disease" refers to a fatal, inherited disorder of the nervous system that begins in childhood. Early symptoms of this disorder typically appear between the ages of 5 and 10. Parents or physicians may notice a previously normal child has begun to develop vision problems or seizures. In some cases the early signs take the form of personality and behavior changes, slow learning, clumsiness, or stumbling. Over time, affected children suffer mental impairment, worsening seizures, and progressive loss of sight and motor skills. Eventually, children with Batten disease become blind, bedridden, and demented. Batten disease is often fatal by the late teens or twenties.

The term "Gaucher Disease" refers to a condition involving a disorder of lipid metabolism that produces an accumulation of glycosphingolipids in so-called Gaucher cells (reticuloendothelial cells). The Gaucher cells fill with glucocerebroside and fibrillar cytoplasm, vary in shape, and have one or several small eccentrically placed nuclei. They are found in the liver, spleen, lymph nodes, and bone marrow. As is known in the art diagnosis may be confirmed by demonstrating the lack of glucocerebrosidase activity in cell culture.

Three major clinical forms are categorized according to differential cellular enzyme deficiency. Type I, the adult chronic normeuronopathic form, is the most common and is typically manifest by hypersplenism, splenomegaly, and bone lesions. Type II, the acute infantile neuronopathic form, is associated with splenomegaly, severe neurologic abnormalities, and death, usually within the first 2 years of life. Type III, the juvenile form, may occur anytime in childhood. Type III combines the features of the adult chronic form with a slowly progressive neurologic dysfunction that is typically milder than seen in the Type II form. Patients who survive to adolescence may live for many years.

The term "Fabry's Disease" refers to a rare, familial, X-linked disorder of lipid metabolism in which glycolipid (galactosylgalactosylglucosyl ceramide) accumulates in many tissues. The disease is typically associated with deficient activity of the lysosomal enzyme β-galactosidase A, which is needed for normal catabolism of trihexosylceramide.

As is known in the art, diagnosis in males is based on appearance of typical skin lesions (angiokeratomas) over the lower trunk. Patients may have corneal opacities, febrile episodes, and burning pain in the extremities. Heterozygous females are usually asymptomatic but may have an attenuated form of disease often characterized by corneal opacities.

The terms "Niemann Pick A and B" or "sphingomyelin lipidoses," refer to lysosomal storage disorders involving a deficiency of sphingomyelinase activity. The disorders are inherited as autosomal recessive traits and appear most often in Jewish families. Type A is characterized by hepatosplenomegaly, failure to thrive, and rapidly progressive neurodegeneration that leads to death by age 2 or 3. Type A patients have less than 5% of normal sphingomyelinase activity. Type B is more variable phenotypically than type A. Xanthomas, skin pigmentation changes, hepatosplenomegaly, and lymphadenopathy may occur. Pancytopenia is common. Sphingomyelinase activity ranges from 5 to 10% of normal. Most patients with type B have little or no neurologic involvement and survive into adulthood. In severe type B, progressive pulmonary infiltrates cause major complications.

The term "Niemann Pick type-C" refers to Niemann-Pick type C is an autosomal recessive, lysosomal lipid storage disease characterized by defective trafficking of intracellular cholesterol and lysosomal accumulation of unesterified cholesterol gangliosides and other lipids. The prevalence of this fatal, childhood-onset, neurodegenerative disease is about 1 in 150,000. Affected individuals have hepatomegaly with foamy macrophage infiltration, chronic neurological deterioration with neuronal accumulation of glycolipids, seizures, supranuclear ophthalmoplegia, and progressively decreasing motor and intellectual function, and they eventually dies in adolescence. NP-C is linked to the NPC1 and NPC2loci. About 95% of human NP-C is caused by mutations of the NPC1 gene, which result in abnormal intracellular trafficking of exogenously and endogenously synthesized cholesterol, leading to the accumulation of unesterified cholesterol and glycosphingolipids; however, the mechanisms that link mutations to the phenotype are unclear. No therapy has been shown to delay the onset of disease or slows its progression.

The term "Schindler Disease" refers to an autosomal recessive neurodegenerative disorder associated with deficient activity of α-N-acetylgalactosaminidase. The disease is an infantile-onset neuroaxonal dystrophy, and presents with the accumulation of sialylated, asialia-glycopeptides, and oligosaccharides. Affected infants have normal development for the first months of life, followed by a rapid neurodegenerative course that ultimately develops into the experience of severe psychomotor retardation, cortical blindness, and frequent myoclonic seizures.

The term "Farber Disease" refers to an autosomal recessive disorder that is associated with deficiency of the lysosomal enzyme, ceramidase. Ceramide accumulatesin various tissues, especially the joints.

The term "Krabbe Disease", "Galactosylceramide lipidosis" or "globoid cell leukodystrophy", refers to a fatal disorder of infants characterized by progressive retardation, paralysis, blindness, deafness, and pseudobulbar palsy. Individuals suffering from this condition have a deficiency of galactocerebroside β-galactosidase. The disorder may be considered both a sphingolipid storage disease and a leukodystrophy The term "Austin Disease" refers to a type of metachromatic leukodystrophy, or multiple sulfatase deficiency, that is a lethal neurodegeneration disorder of infancy. Inheritance is autosomal recessive. diagnosis is made by methods known in the art.

The terms "metachromatic leukodystrophy", "Sulfatide lipidosis", or "Sulfatidosis" refer to a disorder in which deficiency of the enzyme cerebroside sulfatase causes metachromatic lipids to accumulate in the white matter of the CNS, peripheral nerves, kidney, spleen, and other visceral organs. The disease is characterized by progressive paralysis and dementia usually beginning before age 2 and typically resulting in death by age 10.

The term "Fucosidosis" refers to a rare, autosomal recessive disorder results from deficient activity of α-fucosidase and accumulation of fucose containing glycosphingolipids, glycoproteins, and oligosaccharides in lysosomes of the liver, brain, and other organs. Wide variability exists, with severely affected patients presenting in the first year of life. Developmental delay and somatic features are similar to those for mucopolysaccharidoses. These include frontal bossing, hepatosplenomegaly, coarse facial features, and macroglossia. Central nervous system storage results in a relentless neurodegenerative course with death in childhood.

The term "mucopolysaccharidoses" refers to a group of inherited lysosomal storage disorders and with one exception, are inherited as autosomal recessive traits. In individuals with MPS disorders, deficiency or malfunction of specific lysosomal enzymes leads to an abnormal accumulation of certain complex carbohydrates (mucopolysaccharides or glycosaminoglycans) in the arteries, skeleton, eyes, joints, ears, skin, and/or teeth. These accumulations may also be found in the respiratory system, liver, spleen, central nervous system, blood, and bone marrow. This accumulation progressively damages cells, tissues, and various organ systems of the body. There are several different types and subtypes of mucopolysaccharidosis.

Mucopolysaccharidosis type I comprises a deficiency of the enzyme alpha-L-iduronidase. The most severe form of MPS I is often called Hurler syndrome. A milder form of MPS I is called Scheie syndrome. MPS-III (Sanfilippo Syndrome) is subdivided into four types: MPS-III Type A, MPS-III Type B, MPS-III Type C, and MPS-III Type D. All types are associated with some degree of mental deterioration, but the severity depends on the particular type of MPS-III. Several physical defects may be present, and the severity of these defects also varies with the type of MPS-III. Sly syndrome (MPS-VII) is another MPS storage disease caused by a deficiency of the enzyme beta-glucuronidase. The disease is characterized by an accumulation of dermatan sulfate (DS), heparan sulfate (HS) and chondroitin sulfate (CS) in many tissues and organs of the body including the central nervous system.

The term "neurodegenerative disease" refers to a condition in which brain and nervous systems are affected by the deterioration of neurons. Neurodegenerative conditions include conditions causing problems with movements, and conditions affecting memory and conditions related to dementia, or conditions that affect both movement and psychology.

The term "amyotrophic lateral sclerosis" "motor neuron disease", "ALS" or "Lou Gehrig's disease" refers to a neurodegenerative disease that results in loss of motor neurons. Neuronal loss is most striking in the anterior horn cells of spinal cord but may involve cranial motor nuclei and Betz cells. The loss of anterior horn cells leads to muscle atrophy. Astrocytosis is seen in response to the loss of motor neurons. Because of the loss of upper motor neurons, there is lateral column degeneration with gliosis, the so-called "sclerosis" of the lateral columns of spinal cord. Males are affected more commonly than females. Patients typically present in middle age with weakness of the extremities. The course is usually 2 to 6 years after diagnosis. The etiology is unknown.

The term "Huntington's Disease" refers to a neurological disorder inherited in an autosomal dominant manner. The patients usually present between the ages of 20 and 50 years, with a disease course that averages 15 years to death. Patients may either present with choreiform movements, character change, and/or psychotic behavior. The abnormal gene, located on chromosome 4, is called HD, and encodes a protein, called huntingtin. The defective gene contains increased trinucleotide CAG repeat sequences. As is known in the art, genetic tests measure the number of CAG repeats, and the greater the number of repeats, the earlier the onset of the disease. Spontaneous new mutations are uncommon.

The term "demyelinating disorder" refers to disorders of myelination that may be either demyelinating and/or dysmyelinating. Demyelination refers to a condition wherein there is removal or degradation of myelin already formed, whereas dysmyelinating refers to deficient or defective myelin development or maintenance. Demyelinating disorders may be hereditary or acquired, and may affect either or both the peripheral or the central nervous systems. Often diseases of the peripheral nervous system are both demyelinating and dysmyelinating.

The term "Schilder's disease" refers to a rare progressive demyelinating disorder which usually begins in childhood. Symptoms may include dementia, aphasia, seizures, personality changes, poor attention, tremors, balance instability, incontinence, muscle weakness, headache, vomiting, and vision and speech impairment. The disorder is a variant of multiple sclerosis. Schilder's disease is not the same as Addison-Schilder disease (adrenoleukodystrophy).

As with multiple sclerosis, the course and prognosis of Schilder's disease are unpredictable. For some individuals the disorder is progressive with a steady, unremitting course. Others may experience significant improvement and even remission. In some cases, Schilder's disease is fatal.

The term "Guillian-Barre Syndrome" refers to a common acute neuromuscular paralytic syndrome characterized by weakness, parasthesia, hyporeflexia, and sometimes autonomic dysfunction, in severe cases it may lead to respiratory failure. "Guillian-Barre Syndrome" is typically demyelinating, although in some patients some axonal damage may occur. Guillian-Barre Syndrome usually strikes following some other significant medical event, most often an infection. It can occur at any age, and it is somewhat more common among men.

"Guillian-Barre Syndrome" is primarily a motor neuropathy occurring mainly in the peripheral nerves and spinal roots, but it may also involve cranial nerves. "Guillian-Barre Syndrome" presents initially with an ascending symmetrical pattern of progressive weakness, starting in the feet and progressing proximally; it begins in the lower extremities, but the upper limbs soon follow. As the disease progresses, decreased or absent reflexes, hypotonia, ataxia, and paralysis follow, resulting in quadriplegia in 30% of patients. Sensory involvement includes ascending parasthesia and sometimes pain, mainly in lower back and buttocks. If the cranial nerves are involved (45-75% of cases), facial weakness, dysphagia, dysarthria, and difficulty holding up the head may occur. Unlike the peripheral symptoms, facial weakness may be asymmetrical. Autonomic nerve involvement, due to demyelination of the vagus and sympathetic nerves, is evidenced by vital sign lability including respiratory failure, brady/tachycardia, hypo/hypertension, and hypo/hyperthermia, as well as anhidrosis (lack of sweating), paralytic ileus (absent bowel movement), and urinary hesitancy. GBS does not penetrate the blood-brain barrier to enter the CNS, therefore cognitive function remains intact.

Symptoms appear about two weeks following the triggering event. Maximal weakness occurs 2 weeks after the initial onset of symptoms and stops progressing after 4-5 weeks; after that, the patient enters a plateau phase of 2-4 weeks during which there is little change. After that, gradual recovery takes place. The mean recovery time depends upon whether the patient requires mechanical ventilation (about 15-20% of GBS patients do): mean recovery time is 85 days without use of a respirator and 169 days with the respirator. Ultimately the prognosis can range from a best-case scenario of mild walking difficulty with recovery within weeks, to tetraplegia within 24 hours with incomplete recovery after more than 18 months. Full recovery occurs in 50-95% of cases; incidence of permanent neurological sequelae 10-40%, and the mortality rate is 5-10%. Poor prognosis is associated with rapid disease progression, advanced age, ventilation over 1 month, severe slowing or block of NCV, and the presence of antibodies against GM1 (a particular ganglioside). When it occurs, death is usually due to severe autonomic instability (cardiac arrhythmia is especially common in elderly patients), complications of prolonged intubation and paralysis.

The term "leukodystrophy" refers to a group of genetically determined progressive disorders that affect the brain, spinal cord and peripheral nerves.

The term "adrenoleukodystrophy" refers to a progressive, disorder affecting the adrenal gland and the white matter of the nervous system. First recognized in 1923 it has also been known as sudanophilic leukodystrophy. Patients with adrenoleukodystrophy either lack or have a defective form of a protein called ALDP (ALD protein) which is located on the X-chromosome. The defect results in a peroxisomal storage disorder wherein very long chain fatty acids (VLCFA) accumulate in the body tissues, particularly in the brain and the adrenal glands. Ultimately the myelin sheath surrounding the nerves is destroyed causing neurologic problems. Adrenal gland malfunction results in Addison's Disease.

The term "adrenomyeloneuropathy" refers to a milder form of adrenoleukodystrophy which may occur in adolescents or adult men. Major manifestations include, but are not limited to adrenal impairment, varying degrees of difficulty with walking due to spasticity, urinary disturbances and impotence, and sometimes cognitive defects, emotional disturbances and depression. Neurological disability is slowly progressive over several decades. Both adrenoleukodystrophy and Adrenomyeloneuropathy are diagnosed by a blood test to measure the amount of very long chain acids.

The term "Pelizaeus-Merzbacher disease" refers to a nonprogressive, X-linked disorder of the central nervous system (CNS). Pelizaeus-Merzbacher disease differs from other leukodystrophies in that it is a dysmyelinating, rather than a demyelinating condition. The disease is caused by a duplication or mutation of the proteolipid protein gene. Proteolipid protein is the chief protein of the myelin sheaths of the CNS nerve cells. Many different mutations that occur in proteolipid protein may result in Pelizaeus-Merzbacher disease, and the resultant disorders range from very severe ("connatal" PMD), through later onset, intermediate severity ("classical" PMD) to the relatively mild and usually later onset X-linked spastic paraplegia (abbreviated SPG2). The spectrum of disorders may sometimes be referred to as Pelizaeus-Merzbacher disease/X-linked spastic paraplegia or PMD/SPG2.

Initial diagnosis is dependent on the clinical picture of deficiency of white matter in the MRI.

The term "Canavan Disease" refers to a genetically determined leukodystrophy that presents with widespread degeneration of the white matter of the brain. This degeneration leads to swelling and sponginess of the myelin, and sometimes Canavan disease is called "Spongy Degeneration of the Brain" or "van Bogaert-Bertrand Spongy Degeneration of the Brain".

As is known in the art, Canavan diseased may be diagnosed with MRI. The MRI of a child with Canavan disease shows generalized white matter disease with some sponginess. The diagnosis is then confirmed by examining the urine for N-Acetylaspartic acid (NAA). This compound is specific for Canavan disease and it will be more than 100 times the normal levels. An increase of 5-10 times the normal level is not Canavan disease.

The term "Childhood Ataxia with Central Hypomyelination" or "CACH" or "Vanisihing White Matter Disease" refers to a leukodystrophy of unknown etiology. The disease starts in childhood, and after an interval of variable duration, there is sudden onset of a cerebellospastic syndrome. Once initiated, progression is rapid, with severe sudden deteriorations. Most patients develop a progressive gait disorder, speech difficulty or even coma and death between 1 and 5 years of age. Magnetic resonance imaging (MRI) shows extensive involvement of the white matter with the presence of so-called 'cavitated' zones. The cavitated zones resemble the cerebrospinal fluid (CSF) signal on all the MRI. In these cavitated zones, the proton spectrum (NMR spectroscopy) is close to that of the CSF. In addition to these typical forms, other forms start later (adolescence and adulthood), have a slower progression, and individuals may live into the second and third decades.

The term "Alexander Disease" refers to a progressive neurological disorder in which the destruction of white matter in the brain is accompanied by the formation of fibrous, eosinophilic deposits known as Rosenthal fibers. The majority of cases of Alexanders are sporadic; that is, without a known family history of the disorder. The onset of the infantile form of Alexanders disease is usually around six months, but may occur anytime between 0 and 24 months of age. Children who develop Alexanders in infancy generally do not survive past the age of 5 or 6 years. Physical and mental development is retarded, and there is progressive enlargement of the brain and head, increasing spasticity, and seizures in some cases. Histologically, demyelination of both sensory and motor fiber tracts is found. In addition, the eosinophilic Rosenthal fibers are found evenly distributed throughout the brain near blood vessels, and on the surface of the brain. The demyelinated areas do not correspond to the distribution of the Rosenthal fibers. In addition to the infantile form of the disease, juvenile and adult onset forms are recognized, occurring less frequently and with a longer course of progression. These individuals have in common the widespread formation of Rosenthal fibers throughout the central nervous system. Older patients have less white matter loss and have correspondingly milder symptoms.

The term "Refsum Disease" refers to a slowly progressive disorder of lipid metabolism characterized by the accumulation of phytanic acid in blood and tissues and associated with neurologic disorders. Symptoms of the syndrome include, but are not limited to retinitis pigmentosa, peripheral neuropathy, ataxia, and elevated protein in cerebrospinal fluid without pleocytosis. Other characteristics include nystagmus, anosmia, ichthyosis, and epiphyseal dysplasia. Prior to the invention the treatment for Refsum Disease included limiting the "offending" substance, phytanic acid, from the diet. Dietary restrictions of foods containing phytanic acid lowers its plasma concentration. With adherence to diet, peripheral neuropathy is eventually arrested and ichthyosis disappears. However, eye and ear symptoms do not regress, though progression is arrested.

The term "cerebrotendinous xanthomatosis" refers to a leukodystrophy that presents with cataracts, tendon xanthomas (yellowish atty tumors on some tendons), mental retardation, and a progressive neurological deterioration. Patients may develop seizures, emotional or psychiatric disturbances, and motor deficits. Diagnosis of cerebrotendinous xanthomatosis is made by measuring the levels of bile alcohols in blood or urine, or by measuring the level of cholestanol in the blood.

The term "brain cellular metabolism" refers to the totality of biochemical processes that occur in the cells of the brain. A "disruption of brain cellular metabolism" refers to any deviation from the normal baseline functioning of these processes.

The term "hypoglycemia" refers to a condition wherein an individual experiences an abnormally low plasma glucose level. An "abnormally low plasma glucose level" typically occurs when the plasma blood glucose concentration is less than or equal to about 50 mg/dL (2.78 mmol/L) in men, or less than or equal to about 45 mg/dL (2.5 mmol/L) in women. and less than or equal to about 40 mg/dL (2.22 mmol/L) in infants and children.

"Hypoglycemia" may present with t either one of two symptomatic patterns: (a) Adrenergic symptoms which include, but are not limited to sweating, nervousness, tremulousness, faintness, palpitations, and hunger attributed to increased sympathetic activity and epinephrine release; or (b) as CNS manifestations which include, but are not limited to confusion, inappropriate behavior (similar to inebriation), visual disturbances, stupor, coma, and seizures. Hypoglycemic coma commonly causes an abnormally low body temperature.

The term "acidosis" refers to a condition of low arterial pH, reduced plasma $HCO_3^-$ concentration, and usually compensatory alveolar hyperventilation resulting in decreased partial pressure of $CO_2$. The blood hydrogen ion ($H^+$) concentration is maintained within narrow limits. The arterial plasma $H^+$ concentration ranges from 37 to 43 nmol/L ($37 \times 10^{-6}$ to $43 \times 10^{-6}$ mEq/L), and the normal arterial blood pH ranges from 7.37 to 7.43. Metabolic acidosis results when there is an accumulation of acid equivalents in the body. If the acid load overwhelms respiratory capacity, acidemia (arterial pH<7.35) will result. Metabolic acidosis can be due to increased acid production or exogenous acid administration.

The term "hypoxia" refers to a state of oxygen deficiency in the body which is sufficient to cause an impairment of function. Hypoxia may be caused by any number of situations including any situation that reduces partial pressure of oxygen in the blood, including, but not limited to inadequate oxygen transport, or the inability of the tissues to use oxygen. Some of the recognized forms of hypoxia include: anemic or hypemic hypoxia, hypoxic hypoxia, and ischemic or stagnant hypoxia. Anemic or hypemic hypoxia typically results from a reduction in the oxygen carrying capacity of the blood. It may be caused, for example, by a reduction in the amount of hemoglobin in the blood or a reduced number of red blood cells. Hypoxic hypoxia typically results from defective oxygenation of the blood in the lungs and therefore a reduction in the amount of oxygen passing into the blood. Ischemic hypoxia (also called stagnant hypoxia) is an oxygen deficiency that typically results from poor circulation of the blood or poor blood flow. The most common symptom of hypoxia is cyanosis, a bluish cast to the skin, lips and/or fingernails.

The term "hypercarbia" or "hypercapnia" refers to a condition wherein an individual experiences the presence of an abnormally high level of carbon dioxide in the circulating blood. The normal average concentration (partial pressure) of carbon dioxide in the blood is 40 mm Hg. "hypercarbia" or "hypercapnia" occur when the carbon dioxide concentration goes above about 45 mm Hg. Thus, "hypercarbia" occurs when the partial pressure of $CO_2$ in the blood is greater than or equal to about 10% higher than normal, 11% higher, 12% higher, 13 or more percent higher than normal. Symptoms of "hypercarbia" may include, but are not limited to: shortness of breath, headache, delirium, and obtundation.

The expression "other disruption of normal cellular metabolism" refers to any process or event that causes normal cellular processes to be disturbed.

The term "extracellular event" refers to any event or process occurring outside of a cell.

The term "extracellular fluid composition" refers to the composition of that fraction of total body water that is extracellular. The extracellular fluid comprises about ⅓ of the total body water, and about ¾ of the extracellular fluid exists in the interstitial space and connective tissues surrounding cells, whereas about ¼ is intravascular. Extracellular fluid is comprised of characteristic concentrations of ions such as sodium, potassium, magnesium and etc. Normal concentrations of ions and other substances comprising the extracellular fluid are known in the art, and can be found in source books such as The Merck manual of Diagnosis and Therapy, supra.

The term "disruption of extracellular fluid composition" refers to any process or event that changes the composition of the extracellular fluid from its normal, baseline, homeostatic composition. Events that may disrupt extracellular fluid composition may include such events as hyponatremia (see below).

The term "hyponatremia" refers to refers to the condition wherein there is an excess of total body water relative to total body sodium content. Since sodium is the major cation of the extracellular fluid, "hyponatremia" may also be viewed as a condition of having an abnormally low extracellular concentration of sodium ions. The extracellular concentration of sodium ions varies between individuals, but the average extracellular concentration of sodium which is typically in the range of about 140 mEq/L. "Hyponatremia" is typically diagnosed when extracellular sodium concentration drops to about 137 mEq/L or less. Thus, sodium concentration may be considered "abnormally low" when such concentration is 2% lower than the normal concentration, 3% lower, 4% lower, 5% lower, 6 or more percent lower than the average extracellular concentration of sodium.

In contrast to "hyponatremia", the term "hypematremia" refers to the condition of having an abnormally high extracellular concentration of sodium ions. Although "hypernatremia" is less common than "hyponatremia", occurring in less than 1% of all hospitalized patients in acute care hospitals, "hypernatremia" is one of the most serious electrolyte disorders. The condition has a reported mortality of 40 to 60%. Hypernatremia is typically diagnosed when the sodium concentration of the extracellular fluid (plasma) increases to about 145 mEq/L. Thus, the concentration of sodium ions may be considered to be "abnormally high" when the extracellular concentration of sodium ions is about 3% higher than the normal concentration, 4% higher, 5% higher, 6% higher, 7 or more percent higher than the average extracellular concentration of sodium.

Sodium concentration is a major determinant of plasma osmolality, and osmolality can be directly measured my means known to those of skill in the art. The movement of water between the intracellular and extracellular compartments is largely controlled by each compartments' osmolality, since most cell membranes are highly permeable to water. Normally the osmolality of the extracellular fluid, which is about 290 mOsm/kg water, on average, is about equal to the osmolality of the intracellular fluid.

Osmolality is normally maintained within narrow limits. When the osmolality of the extracellular fluid increases above normal levels a condition known as "hyperosmolality" of the extracellular fluid develops. In contrast to hyperosmolality, "hypoosmolality" of the extracellular fluid refers to a state wherein the osmolality of the extracellular fluid is lower than normal levels.

As is known in the art, normal total calcium concentration of the plasma is between about 8.8 to about 10.4 mg/dL (i.e., about 2.20 mmol/L to about 2.60 mmol/L). Thus, the term "hypercalcemia" refers to a condition wherein the concentration of calcium is above about 10.4 mg/dL. In contrast to "hypercalcemia", the term "hypocalcemia" refers to a condition wherein the plasma protein concentration is normal, but the total plasma (extracellular fluid) concentration of calcium is below about 8.8 Ing/dL.

The metabolism of calcium and phosphate are intimately related.

As is known in the art, the normal adult plasma inorganic phosphate ($PO_4$) concentration is between about 2.5 mg/dL to about 4.5 mg/dL. Phosphate concentration is about 50% higher in infants, and about 30% higher in children.

The term "hyperphosphatemia" refers to a condition wherein the adult plasma inorganic phosphate concentration is above about 4.5 mg/dL. In contrast to "hyperphosphatemia" the term "hypophosphatemia" refers to a condition wherein the adult plasma inorganic phosphate concentration is below about 2.5 mg/dL.

The normal plasma magnesium concentration ranges from about 1.4 mEq/L to about 2.1 mEq/L (i.e., 0.7 to about 1.05 mmol/L). The term "hypermagnesemia" refers to a condition wherein the plasma magnesium concentration is abnormally high, typically above about 2.1 mEq/L. In contrast to hypermagnesemia, the term "hypomagnesemia" refers to a condition wherein the plasma magnesium concentration is abnormally low, typically below about 1.4 mEq/L. Clinical manifestations of "hypomagnesemia" may include, but are not limited to anorexia, nausea, vomiting, weakness personality changes, tremor and seizures. Neurologic symptoms may also be associated with concomitant hypocalcemia and hypokalemia.

The term "psychiatric condition" refers to any deviation from normal mental functioning. Psychiatric conditions are well known to those of kill in the art. Symptomatic and diagnostic criteria can be found in the DSM-IV-TR, supra.

The term "frontotemporal dementias" refers to a set of degenerative condition of the front (anterior) part of the brain resulting in progressive loss of cognitive and intellectual functions (dementia). Presentation typically comprises either (a) gradual and progressive changes in behavior or (b) gradual and progressive language dysfunction. "Frontotemporal Dementias" include, but are not limited to Frontotemporal Dementia, Semantic Dementia, and Progressive Non-Fluent Aphasia. Frontotemporal dementia is a focal form of dementia, which is clinically and pathologically distinct from other dementias. Diagnosis can be made by any method available to those of skill in the art (see e.g., DSM-IV-TR (American Psychiatric Association: *Diagnostic and Statistical Manual of Mental Disorders*, Fourth Edition, Text Revision, Washington D.C., American Psychiatric Association (2000), *The Merck Manual of Diagnosis and Therapy* 17th Edition (1999) and Snowden J. S., et al., *The British Journal of Psychiatry*, 180: 140-143 (2002)).

The term "movement disorders" refers to conditions involving abnormalities in muscle tone and motor control. "Movement disorders include but are not limited to: Ataxia, Blepharospasm, Dysphonia, Gait disorders, Huntington's disease, Myoclonus, Parkinson's disease, Tardive dyskinesia, Tics and Tourette syndrome and Tremor.

The term "psychosis" refers to a psychiatric symptom, condition, or syndrome in its broadest sense, as defined in the DSM-IV-TR (American Psychiatric Association: *Diagnostic and Statistical Manual of Mental Disorders*, Fourth Edition, Text Revision, Washington D.C., American Psychiatric Association (2000)), comprising a "psychotic" component, as broadly defined below. The term psychosis can refer to a symptom associated with a general medical condition, a disease state or other condition, such as a side effect of drug abuse (a substance-induced disorder) or as a side effect of a medication. Alternatively, the term psychosis can refer to a condition or syndrome not associated with any disease state, medical condition, drug intake or the like. Psychosis is typically defined as a mental disorder or condition causing gross distortion or disorganization of a person's mental capacity, affective response, or capacity to recognize reality, communicate, and relate to others to the degree of interfering with their capacity to cope with the ordinary demands of everyday life.

The term "psychotic" refers to a condition that may include delusions or prominent hallucinations, including prominent hallucinations that the individual realizes are hallucinatory experiences, and those with hallucinations occurring in the absence of insight into their pathological nature. Finally, the term includes a psychotic condition characterized by a loss of ego boundaries or a gross impairment in reality testing.

Objective tests can be also be used to determine whether an individual is psychotic and to measure and assess the success of a particular treatment schedule or regimen. For example, measuring changes in cognitive ability aids in the diagnosis and treatment assessment of the psychotic patient. Any test known in the art can be used, such as the so-called "Wallach Test," which assesses recognition memory (see below, Wallach, *J. Gerontol.* 35: 371-375 (1980)), or the Stroop Color and Word Test ("Stroop Test") (see Golden, C. J., Cat. No. 30150M, In: *A Manual for Clinical and Experimental Uses*, Stoelting, Wood Dale, Ill.).

The term "schizophrenia" refers to a psychiatric condition that makes it difficult for a person to tell the difference between real and unreal experiences, to think logically, to have normal emotional responses to others, and to behave normally in social situations. There are 5 recognized types of schizophrenia: catatonic, paranoid, disorganized, undifferentiated, and residual. As is well known in the art, people with schizophrenia may show a variety of symptoms. As the illness progresses, psychotic symptoms may develop. Psychotic symptoms associated with schizophrenia may include, but are not limited to delusions, hallucinations, disordered thinking, catatonic behavior, and flat affect. Further symptomatic and diagnostic criteria for schizophrenia c can be found in the DSM-IV-TR, supra.

The term "alcoholism" refers to a condition characterized by deviant behaviors associated with the prolonged consumption of excessive amounts of alcohol. Consumption of large amounts of ethanol usually, but not always causes clinical toxicity and tissue damage, physical dependence, and a dangerous withdrawal syndrome. The term "alcoholism" also refers to social impairment in the lives of alcoholics and their families. An alcoholic is identified by severe dependence or addiction and a cumulative pattern of characteristic behaviors that include, but are not limited to, obvious and frequent intoxication that is destructive in that it interferes with a person's ability to socialize and work. Eventually drunkenness may lead to failed relationships and job loss. Alcoholics may incur physical injury, be apprehended for drunk driving, or drunkenness. Eventually they may be hospitalized for delirium tremons or cirrhosis.

The term "posttraumatic stress disorder" refers to refers to a psychiatric condition in its broadest sense, as defined in DSM-IV-TR (2000, supra). The DSM-IV-TR defines "Post-Traumatic Stress Disorder" as characterized by persistent re-experiencing of an extreme traumatic event. The DSM-IV-TR sets forth a generally accepted standard for diagnosing and categorizing Post-Traumatic Stress Disorder.

The term "social isolation" refers to perceived social isolation as measured by the UCLA loneliness scale (Russel et al., *J. Pers. Soc. Psychol.*, 39:472-480 (1980)).

The term "Liver X Receptor ligand" or "LXR ligand" refers to agonists and antagonists that bind the Liver X Receptor. One group of LXR ligands includes the "oxysterols". Oxysterols are cholesterol derived steroid molecules that include TO901317, 22(R)-hydroxycholesterol, 24(S)-hydroxycholesterol, 24(S),25-epoxycholesterol, and 27-hydroxycholesterol.

As used herein, "pharmaceutically acceptable carrier" includes any material, which when combined with the compound of the invention retains the compound's activity and is non-reactive with the subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

Introduction

The present invention relates to the surprising discovery that treatment of central nervous system disorders can be effected by the administration of neuroactive steroids to a patient in need thereof. Further, the invention relates to the discovery that the administration of neuroactive steroids, in combination with a LXR ligand provides effective treatment for a wide variety of neurological disorders including brain diseases, neurodegenerative diseases, and congenital storage diseases. Thus, the invention is directed toward the treatment of a broad group of neurological disorders with a novel class of drugs.

For purposes of illustration, the invention is described with frequent reference to Niemann Pick type-C disease as an exemplary disorder, and allopregnanolone as an exemplary drug. The description is for clarity of illustration, and is not intended to define or limit the scope of the present invention.

Allopregnanolone treatment of Niemann Pick type-C mice substantially reduces gangliosides GM1, GM2 and GM3 in the brain. Thus, allopregnanolone is effective for the treatment of ganglioside storage diseases.

However, the effectiveness of allopregnanolone and related compounds is not limited to the treatment of ganglioside storage diseases. Indeed, such compounds are also useful for the treatment of neurodegenerative diseases. For example, treatment of cerebellar cells in culture with allopregnanolone, increases the concentrations of the neurotrophins NGF and BDNF. These factors support the growth and maintenance of neurons in the central nervous system. Thus, individuals suffering from neurodegenerative disorders, wherein levels of NGF decrease with the progression of the disease e.g., Parkinson and Alzheimer, will benefit from the methods of the invention.

In addition, increased production of NGF and other trophic factors in the central nervous system can suppress inflammation in diseases such as multiple sclerosis. Indeed, allopregnanolone ameliorates CNS inflammatory responses in treated mice. Untreated Niemann Pick type-C mice have an abnormal immune response in their brains, characterized by changes in the permeability of the blood brain barrier, and appearance of T cells and activated macrophages. In mice treated with allopregnanolone, there is a significant reduction in the number of T cells and activated macrophages. There is also a substantial reduction in the brain concentrations of certain cytokines that is associated with this immune response, and reduction of apoptotic neurons. Thus, allopregnanolone and related compounds are effective for the treatment of central nervous system inflammatory disorders.

As will be clear from the detailed description that follows, the invention provides treatment for a wide variety of neurological disorders by providing methods for administration of neuroactive steroids including allopregnanolone and other structurally related compounds. For example the structurally related neurosteroid, ganaxolone, which is the 3-methyl derivative of allopregnanolone also shows efficacy in the treatment of neurological conditions. Ganaxolone increases survival of Niemann Pick type-C mice, delays weight loss and tremor in the mice, and delays loss of coordination and locomotion typically observed in the Niemann Pick type-C mice.

Thus, in one aspect the invention provides a method for treatment of a nervous system condition comprising administering to a patient in need thereof, an effective amount of a composition comprising a compound having a structure according to Formula (I) above.

In a second aspect, the invention provides a method for treatment of a nervous system condition comprising administering to a patient in need thereof, a composition comprising an effective amount of a LXR ligand in combination with an effective amount of a neuroactive steroid compound having a structure according to Formula (I).

As the methods of the invention include use of any neuroactive steroid that is structurally related to allopregnanolone, as such, illustrative compounds and compositions which can be used to ameliorate the symptoms and signs of neurological disease in a subject are set forth. Routine procedures that can be used to identify further compounds and compositions of use in practicing the methods of the invention are also described. As the invention provides for administering these compounds and compositions as pharmaceuticals, routine means to determine neurosteroid drug regimens and formulations to practice the methods of the invention are set forth below.

The Embodiments

I. Diagnosis of a Nervous System Condition in a Subject

Means to diagnosis a nervous system condition are known in the art and include classical, clinical and psychological evaluations, which can be augmented by various laboratory procedures. Such means are well-described in the medical, scientific and patent literature (see e.g., The Merck Manual of Diagnosis and Therapy, Seventeenth Edition, Beers, M. H. and Berkow, R. eds. (1999); *The Patholoic Basis of Disease*, Vinay Kumar, Nelson Fausto, Abul K. Abbas eds. (2004); and the DSM IV-TR, supra). Some illustrative examples are also provided below.

Niemann-Pick Type-C is initially diagnosed by taking a small piece of skin ("skin biopsy"), growing the cells ("fibroblasts") in the laboratory, and then studying their ability to transport and store cholesterol. The transport of cholesterol in the cells is studied by measuring conversion of the cholesterol from one form to another ("esterification"). The storage of cholesterol is assessed by staining the cells with a compound ("filipin") which glows under ultraviolet light. Typically, both the transport and storage tests are performed, to ensure that the diagnosis is correct.

II. Compositions of the Invention

The present invention provides methods of treating a nervous system condition in a subject utilizing compositions comprising neuroactive steroids. In some embodiments, the invention provides compositions comprising a neuroactive steroid in combination with a LXR ligand. Neuroactive steroids and LXR ligands utilized in the methods of the invention are well described in the scientific literature. A few illustrative examples are set forth below.

A. Neuroactive Steroids

In one aspect the invention provides a method for treatment of a nervous system condition comprising administering to a patient in need thereof, an effective amount of a composition comprising a compound having a structure according to Formula (I) above.

In an exemplary embodiment, allopregnanolone is administered to treat a subject and ameliorate the symptoms of a nervous system condition.

In other exemplary embodiments, neuroactive steroids that are structurally related to allopregnanolone are administered to a subject to ameliorate the symptoms of a nervous system condition. Neuroactive steroids are obtained by modification of the basic structure of allopregnanolone, i.e., variation on forms of the steroid backbone. In one exemplary embodiment, ganaxolone is provided to a subject to ameliorate the symptoms of a nervous system condition.

Further examples of neuroactive steroids that are structurally related to allopregnanolone include, but are not limited to, various ester, oxime, and thiazolidine derivatives of 3-hydroxylated-5-reduced-20-ones, 3α5α tetrahydroprogesterone; 5α pregnan-3α hydroxy-20-one or any derivatives and/or 5β isomers of the basic structures such as 5β-pregnan-3α-ol-20-one; and their physiological esters and salts.

B. Liver X Receptor (LXR) Ligands

Aspects of the present invention make use of compositions comprising LXR ligands. The Liver X Receptor (LXRα and LXRβ) is a nuclear receptor activated by oxysterols and also some non-oxysterols. In some exemplary embodiments, methods of the invention employ compositions that comprise LXR ligands, and in other exemplary embodiments, the methods of the invention comprise LXR ligands in combination with a neuroactive steroid.

In one embodiment the LXR ligand is an oxysterol. In exemplary embodiments the oxysterol is selected from TO901317, 22(R)-hydroxycholesterol, 24(S)-hydroxycholesterol, 24(S),25-epoxycholesterol, or 27-hydroxycholesterol.

In other exemplary embodiments, the LXR ligand is a non-oxysterol e.g., Paxilline.

III. Treating a Nervous System Condition in a Subject Using Neuroactive Steroids Neuroactive steroids, such as allopregnanolone, are formulated as pharmaceuticals to be used in the methods of the invention to treat a nervous system condition in a subject. It is understood that a subject receiving treatment for a nervous system condition according to the methods of the invention is not otherwise in need of treatment with a neuroactive steroid composition of the invention. The phrase "not otherwise in need of treatment with a neuroactive steroid composition of the invention" means that a subject is not suffering from any condition known in the art to be effectively treatable with a neuroactive steroid of the invention nor a composition of the invention comprising a neuroactive steroid in combination with a LXR ligand. Some exemplary conditions known in the art to be treatable with a neuroactive steroid or a composition comprising a neuroactive steroid in combination with a LXR ligand include: stress, anxiety, insomnia, depression, epilepsy and seizure activity, premenstrual syndrome, premature labor, hypertension, cardiovascular problems associated with oral contraception and postnatal depression.

In general, any composition comprising a compound that is structurally related to allopregnanolone as disclosed herein can be used as a pharmaceutical in the invention. Routine means to determine neuroactive steroid drug regimens and formulations to practice the methods of the invention are well described in the patent and scientific literature, and some illustrative examples are set forth below.

A. Neuroactive Steroids as Pharmaceutical Compositions

The neuroactive steroids used in the methods of the invention can be administered by any means known in the art, e.g., parenterally, topically, orally, or by local administration, such as by aerosol or transdermally. The methods of the invention provide for prophylactic and/or therapeutic treatments. The neuroactive steroids as pharmaceutical formulations can be administered in a variety of unit dosage forms depending upon the condition or disease and the stage and extent of the disease, the general medical condition of each patient, the resulting preferred method of administration and the like. Details on techniques for formulation and administration are well described in the scientific and patent literature, see, e.g., the latest edition of Remington's Pharmaceutical Sciences, Mack Publishing Co, Easton Pa. ("Remington's"). Therapeutically effective amounts of neuroactive steroids suitable for practice of the method of the invention will typically range from about 0.5 to about 25 milligrams per kilogram (mg/kg). A person of ordinary skill in the art will be able without undue experimentation, having regard to that skill and this disclosure, to determine a therapeutically effective amount of a particular glucocorticoid blocker compound for practice of this invention. For example, a particular neuroactive steroid may be more effective at higher or lower doses. By evaluating a patient using the methods described herein, a skilled practitioner will be able to determine whether a patient is responding to treatment and will know how to adjust the dosage levels accordingly.

In general, neuroactive steroid compounds may be administered as pharmaceutical compositions by any method known in the art for administering therapeutic drugs. Compositions may take the form of tablets, pills, capsules, semisolids, powders, sustained release formulations, solutions, suspensions, elixirs, aerosols, or any other appropriate compositions; and comprise at least one compound of this invention in combination with at least one pharmaceutically acceptable excipient. Suitable excipients are well known to persons of ordinary skill in the art, and they, and the methods of formulating the compositions, may be found in such standard references as Alfonso A R: Remington's Pharmaceutical Sciences, 18th ed., Mack Publishing Company, Easton Pa. (1990). Suitable liquid carriers, especially for injectable solutions, include water, aqueous saline solution, aqueous dextrose solution, and glycols.

Aqueous suspensions of the invention comprise a neuroactive steroid in admixture with excipients suitable for the manufacture of aqueous suspensions. Such excipients may include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending a neuroactive steroid in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

Neuroactive steroid pharmaceutical formulations can be prepared according to any method known to the art for the manufacture of pharmaceuticals. Such drugs can contain sweetening agents, flavoring agents, coloring agents and preserving agents. Any neuroactive steroid formulation can be admixtured with nontoxic pharmaceutically acceptable excipients which are suitable for manufacture.

Typically, neuroactive steroid compounds suitable for use in the practice of this invention will be administered orally. The amount of a compound of this invention in the composition may vary widely depending on the type of composition, size of a unit dosage, kind of excipients, and other factors well known to those of ordinary skill in the art. In general, the final composition may comprise from 0.000001 percent by weight (% w) to 15% w of the neuroactive steroid compounds, preferably 0.00001% w to 1.5% w, with the remainder being the excipient or excipients. For example, the neuroactive steroid allopregnanolone is given orally in tablet form, with dosages in the range of between about 10 and 100 mg/kg, more preferably between about 20 mg/kg and 60 mg/kg, most preferably about 35 mg/kg. The dosage may be provided a single daily dose or in several smaller doses once or twice a day.

Pharmaceutical formulations for oral administration can be formulated using pharmaceutically acceptable carriers well known in the art in dosages suitable for oral administration. Such carriers enable the pharmaceutical formulations to be formulated in unit dosage farms as tablets, pills, powder, dragees, capsules, liquids, lozenges, gels, syrups, slurries, suspensions, etc. suitable for ingestion by the patient. Pharmaceutical preparations for oral use can be obtained through combination of neuroactive steroid compounds with a solid excipient, optionally grinding a resulting mixture, and processing the mixture of granules, after adding suitable additional compounds, if desired, to obtain tablets or dragee cores. Suitable solid excipients are carbohydrate or protein fillers and include, but are not limited to sugars, including lactose, sucrose, mannitol, or sorbitol; starch from corn, wheat, rice, potato, or other plants; cellulose such as methyl cellulose, hydroxypropylmethylcellulose or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

The neuroactive steroids of this invention can also be administered in the form of suppositories for rectal administration of the drug. These formulations can be prepared by mixing the drug with a suitable non-irritating excipient which is solid at ordinary temperatures but liquid at the rectal temperatures and will therefore melt in the rectum to release the drug. Such materials are cocoa butter and polyethylene glycols.

The neuroactive steroids of this invention can also be administered by in intranasal, intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995).

The neuroactive steroids of the invention can be delivered transdermally, by a topical route, formulated as applicator sticks, solutions, suspensions, emulsions, gels, creams, ointments, pastes, jellies, paints, powders, and aerosols.

The neuroactive steroids of the invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles,

*J. Pharm. Pharmacol.* 49:669-674, 1997). Both transdermal and intradermal routes afford constant delivery for weeks or months.

The neuroactive steroid pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5, that is combined with buffer prior to use.

In another embodiment, the neuroactive steroid formulations of the invention are useful for parenteral administration, such as intravenous (IV) administration. The formulations for administration will commonly comprise a solution of the neuroactive steroid (e.g., allopregnanolone) dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of neuroactive steroid in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the neuroactive steroid formulations of the invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the neuroactive steroid into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

B. Determining Dosing Regimens for Neuroactive Steroids

The methods of this invention treat nervous system disorders in a subject e.g., a patient. The amount of neuroactive steroid adequate to accomplish this is defined as a "therapeutically effective dose". The dosage schedule and amounts effective for this use, i.e., the "dosing regimen," will depend upon a variety of factors, including the severity of the disease, the patient's physical status, age and the like. In calculating the dosage regimen for a patient, the mode of administration also is taken into consideration.

The dosage regimen also takes into consideration pharmacokinetics parameters well known in the art, i.e., the neuroactive steroids' rate of absorption, bioavailability, metabolism, clearance, and the like (see, e.g., Hidalgo-Aragones, J. Steroid Biochem. Mol. Biol. 58:611-617, (1996); Groning, Pharmazie 51:337-341, (1996); Fotherby, Contraception 54:59-69, (1996); Johnson, J. Pharm. Sci. 84:1144-1146, (1995); Rohatagi, Pharmazie 50:610-613, (1995); Brophy, Eur. J. Clin. Pharmacol. 24:103-108, (1983); *Remington's Pharmaceutical Sciences,* 18th Ed. (Alfonso R. Gennaro, ed.; Mack Publishing Company, Easton, Pa., (1990); Remington: the Science and Practice of Pharmacy 19$^{th}$ Ed. (Lippincott, Williams & Wilkins, (1995)). The state of the art allows the clinician to determine the dosage regimen for each individual patient, neuroactive steroid and disease or condition treated. As an illustrative example, the guidelines provided below for allopregnanolone can be used as guidance to determine the dosage regimen, i.e., dose schedule and dosage levels, of any neuroactive steroid administered when practicing the methods of the invention.

Single or multiple administrations of neuroactive steroid formulations can be administered depending on the dosage and frequency as required and tolerated by the patient. The formulations should provide a sufficient quantity of active agent, e.g., allopregnanolone, to effectively ameliorate a nervous system disorder in a subject. For example, a typical exemplary pharmaceutical dosage for subcutaneous administration of a neuroactive steroid such as allopregnanolone would be about 5 to about 50 mg/kg of body weight per patient per day. In another exemplary embodiment, pharmaceutical dosage for subcutaneous administration would be between about 10 to about 40 mg/kg of body weight per patient per day, and in another exemplary embodiment the pharmaceutical dosage would be 25 mg/kg of body weight per patient per day, although dosages of between about 1 to about 75 mg/kg of body weight per day may be used in the practice of the invention.

Similarly, when formulating the dosage for a composition comprising a LXR ligand, a typical oral dosage of the ligand, given in tablet form, might range between about 25 and 100 mg/kg, alternatively between about 40 mg/kg and 60 mg/kg, or about 50 mg/kg, although dosages between about 10 mg/kg to about 125 mg/kg are acceptable for the practice of the invention.

Lower dosages can be used, particularly when the drug is administered to an anatomically secluded site, such as the cerebral spinal fluid (CSF) space, in contrast to administration orally, into the blood stream, into a body cavity or into a lumen of an organ. Substantially higher dosages can be used in topical administration. Actual methods for preparing parenterally administrable neuroactive steroid formulations will be known or apparent to those skilled in the art and are described in more detail in such publications as Remington's, supra. See also: Nieman, In *"Receptor Mediated Antisteroid Action,"* Agarwal, et al., eds., De Gruyter, New York, 1987.

After a pharmaceutical comprising a neuroactive steroid of the invention has been formulated in a acceptable carrier, it can be placed in an appropriate container and labeled for treatment of an indicated condition. For administration of neuroactive steroid, such labeling would include, e.g., instructions concerning the amount, frequency and method of administration. In one embodiment, the invention provides for a kit for treating a nervous system disorder in a subject which includes a neuroactive steroid and instructional material teaching the indications, dosage and schedule of administration of the neuroactive steroid.

It is understood that the examples and embodiments described herein are for illustrative purposes only and that various modifications or changes in light thereof will be suggested to persons skilled in the art and are to be included within the spirit and purview of this application and scope of the appended claims.

All publications and patent applications cited in this specification are herein incorporated by reference as if each individual publication or patent application were specifically and individually indicated to be incorporated by reference.

EXAMPLES

The following examples are provided to illustrate the compositions and methods of the present invention, but are not meant to limit the claimed invention.

Materials and Methods

The materials and methods used for the following experiments have been described in Griffin L. D., et al., Nature Medicine 10: 704-711 (2004). This reference is hereby incorporated by reference in its entirety.

Example 1

Allopregnanolone Treatment of Niemann Pick Type-C Mice Substantially Reduces Accumulation of the Gangliosides GM1, GM2, and GM3 in the Brain Mice were given a single injection of allopregnanolone, prepared in 20% βcyclodextrin in phosphate buffered saline, at a concentration of 25 mg/kg. The injection was on day 7 of life (P7, postnatal day 7). Concentrations of gangliosides GM1, GM2, GM3, were measured as well as other lipids such as ceramides and cerebrosides.

Figure 1:
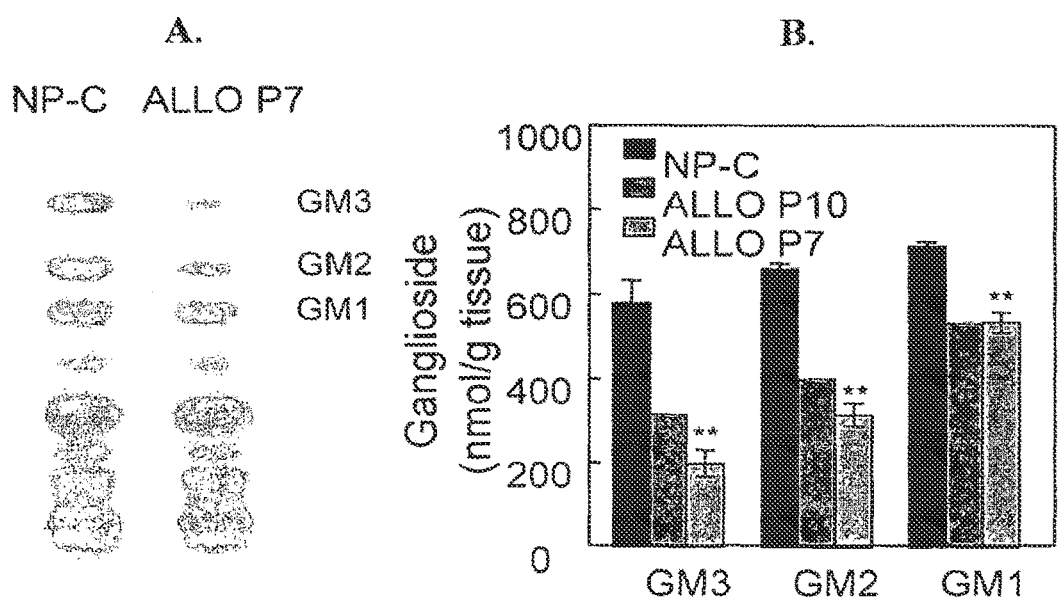
FIG. 1: Ganglioside profiles in cortex from Neimann Pick type-C (NP-C) mice treated with allopregnanolone. (a) High-performance TLC profile of gangliosides from untreated (left) and day 7-treated (right) NP-C mice. (b) Quantitative data for gangliosides GM2, GM3 and GM1 in the cortex from untreated, day 10- and day-7-treated NP-C mice. Individual gangliosides are expressed as nanomoles of ganglioside per gram of wet weight of tissue (n=3 untreated, n=2 day 10-treated, and n=4 day 7-treated NP-C mice; data are the mean±s.d.; **P<0.001).
Figure 2:
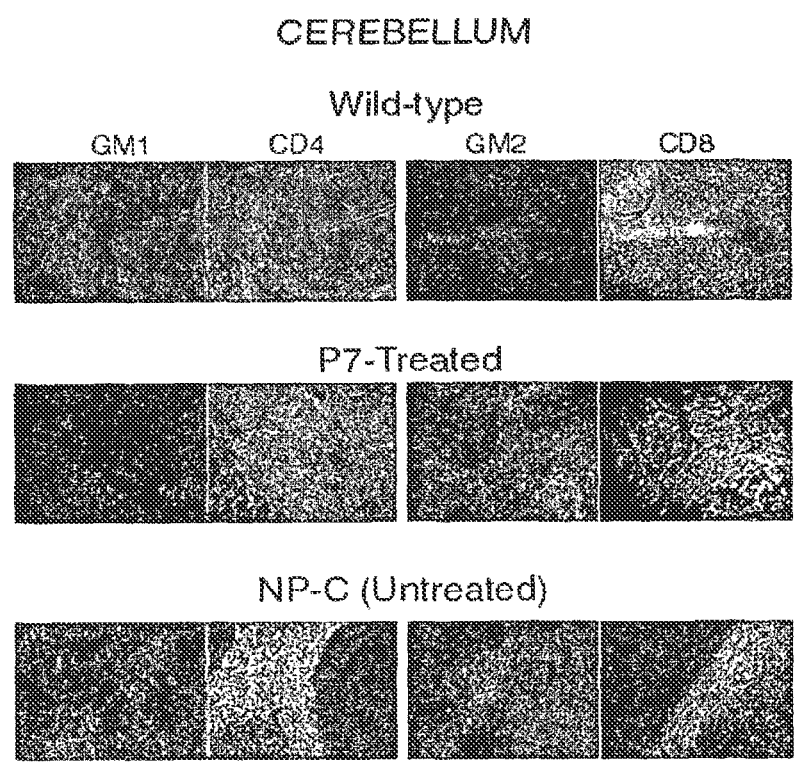
FIG. 2: Immunostaining for gangliosides GM1 and GM2, and for $CD4^+$ and for $CD8^+$ T cells in adult (60-day old) mouse brains. Cerebellum. There is virtually no GM1 or GM2 immunostaining in wild type mouse cerebella, and only slight immunostaining in allopregnanolone-treated mice, while there is GM1 and GM2 immunostaining in untreated NP-C mice. This coincides with a large increase in immunostaining for CD4 and CD8 T cells, seen in the untreated NP-C mice, but absent from both P7 allopregnanolone-treated NP-C mice and wild type mice.
Figure 3:
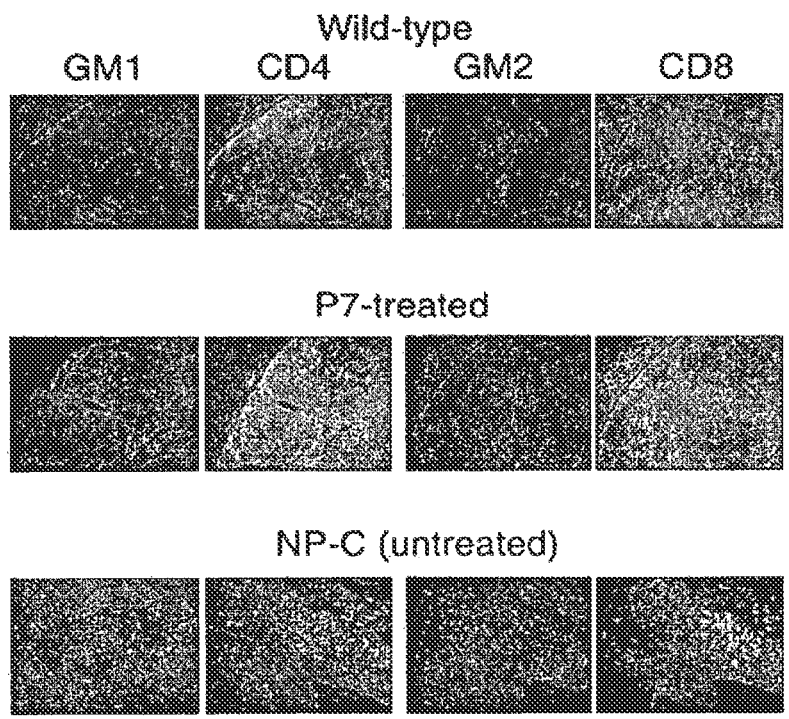
FIG. 3: Immunostaining for gangliosides GM1 and GM2, and for $CD4^+$ and for $CD8^+$ T cells in adult (60-day old) mouse brains. Thalamus/hypothalamus. There is virtually no GM1 or GM2 immunostaining in the thalamus/hypothalamic region of wild type mouse, and only very slight immunostaining in P7-allopregnanolone-treated mice, while there is GM1 and GM2 immunostaining in untreated NP-C mice. This coincides with a large increase in immunostaining for CD4 and CD8 T cells, seen in the untreated NP-C mice, but absent from both P7 allopregnanolone-treated NP-C mice and wild type mice.

As can be seen in FIG. 1, FIG. 2, and FIG. 3 the amount of the gangliosides GM1, GM2, and GM3 were reduced in treated mice, compared with the concentrations in untreated controls. This result was seen in every area of the brain investigated.

The degree of reduction depends upon the timing of the allopregnanolone treatment, with earlier treatment at postnatal day 7 producing greater reduction in the gangliosides, than treatment at postnatal day 10. Therefore, allopregnanolone treatment is effective to ameliorate the symptoms of ganglioside storage diseases e.g., Tay Sachs, Batten, Sandhoff, Gaucher, Niemann Pick A and B, Fabry.

Example 2

Allopregnanolone Treatment of Niemann Pick Type-C Mice Ameliorates Inflammatory Responses in the Central Nervous System Untreated NP-C mice have an abnormal immune response in their brains, characterized by changes in the permeability of the blood brain barrier, and appearance of T cells and activated macrophages.

Mice were again given a single injection of allopregnanolone, prepared in 20% β-cyclodextrin in phosphate buffered saline, at a concentration of 25 mg/kg. The injection was on day 7 of life (P7, postnatal day 7). Inflammation was measured by assessing the number of $CD4^+$ $CD8^+$, $MAC1^+$, and $MHCII^+$ cells, using immunocytochemistry. Concentrations of brain cytokines were also measured, using by enzyme linked immunoabsorbent (ELISA) assays.

Figure 4:
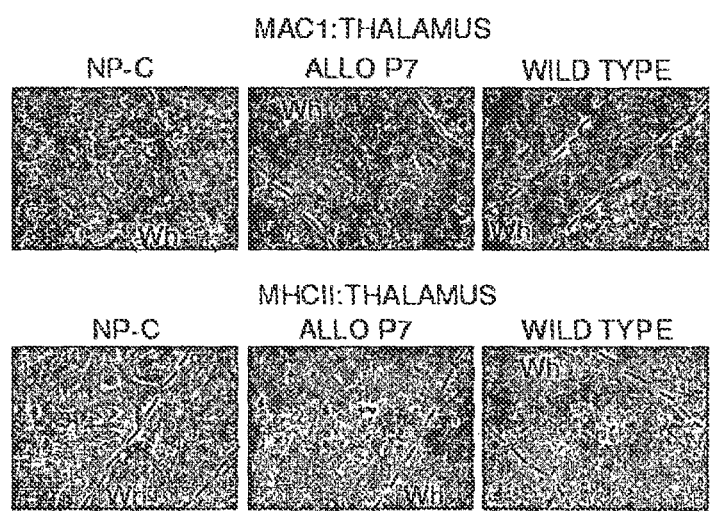
FIG. 4: Immunostaining for MAC1 and for MHCII activated macrophage cells in adult (60-day old) mouse brains.

As can be seen in FIG. 4 and FIG. 5, compared with the untreated controls, mice treated with allopregnanolone at postnatal day 7, show a significant reduction in the number of T cells and activated macrophages in their brains. There is also a substantial reduction in the brain concentrations of certain cytokines that are associated with this immune response. Finally, there is a substantial reduction of apoptotic neurons in the brains of allopregnanolone-treated mice. Therefore, allopregnanolone treatment is effective for the treatment of central nervous system inflammatory disorders. These disorders include, but are not limited to Multiple Sclerosis, Alzheimer's Disease, Parkinson's Disease, spinal cord injury, ischemia and stroke.

Example 3

Allopregnanolone Treatment of Cerebellar Cells in Culture Increases the Concentrations of the Neurotrophins NGF and BDNF NGF and BDNF are important for the growth and maintenance of neurons in the central nervous system. Neurodegenerative disorders, especially Parkinson and Alzheimer, are accompanied by changes in the levels of NGF that reflect the extent to which the disease has progressed. Increased production of NGF and other trophic factors in central nervous system during diseases such as multiple sclerosis can suppress inflammation. Thus, trophic factors in the CNS protects axons and myelin and actively contribute to the maintenance of the brain immune privilege.

Pure cultures of cerebellar astrocytes from P3 cerebella were cultured for 1-3 days±10 nM allopregnanolone, and NGF was assayed every 24 hr by ELISA. As can be seen in FIG. 6, treatment of the cultured NP-C mouse cells in the presence of allopregnanolone increases production of NGF by comparison to the untreated control cells.

Example 4

Ganaxolone Treatment of Neimann Pick Type-C Mice Increases Survival, Delays Weight Loss, Tremor, Loss of Coordination and Locomotion in the Mice Mice were given a single injection of ganaxolone, prepared in 20% β-cyclodextrin in phosphate buffered saline, at a concentration of 25 mg/kg. The injection was on day 7 of life (P7, postnatal day 7).

Efficacy of treatment was assessed by measuring body weight, neurological symptoms, using behavioral tests such as wire hang test, rope climbing test, walking on an mesh inclined plane, and walking on a horizontal surface, measuring coordination, use of all 4 limbs, posture, tail placement. Efficacy was also assessed by measuring lifespan. Results of these experiments are summarized below, and are shown graphically in FIG. 7.

Lifespan: Untreated NP-C mice lived an average of 67 days (±10). Mice treated with ganaxolone lived average of 118 days (±13).

Weight: Untreated NP-C mice gain weight at a rate identical to wild type mice for about 6 weeks; at 6 weeks however, they begin to lose weight, and this weight loss is rapid, continuing over the next 3-4 weeks, after which they die. By contrast, mice treated with ganaxolone do not lose weight as rapidly as the untreated mice. Mice treated at P7 with a single injection of ganaxolone did not begin to lose weight until 10 weeks, and then, lost weight more slowly than untreated NP-C mice.

Locomotor skills: Untreated NP-C mice begin to lose locomotor function beginning at 6-7 weeks of age, and continue this loss of function for the next 3-4 weeks of life. Mice treated with ganaxolone do not begin to lose motor function (locomotion and coordination) until 10 weeks of age. The loss of motor function is also more gradual, occurring over the course of 5 weeks.

Thus, like treatment with allopregnanolone, ganaxolone also increases survival in NP-C mice, delays weight loss and tremor in the mice, and delays loss of coordination and locomotion in the NP-C mice.

Example 5

Treatment of Niemann Pick Type-C Mice with Allopregnanolone in Combination with an Oxysterol LXR Ligand Extends Life Span and Delays Onset of Neurological Symptoms to a Greater Degree than Either Drug Alone Mice were given a single injection of allopregnanolone, prepared in 20% β-cyclodextrin in phosphate buffered saline, at a concentration of 25 mg/kg. The injection was on day 7 of life (P7, postnatal day 7). T0901317 treatment was started on day 18 (50 mg/kg/day) in chow. Efficacy was assessed by measuring body weight, and neurological symptoms, using a rotorod test. Efficacy was further assessed by measuring lifespan.

Lifespan: Untreated NP-C mice lived an average of 67 days. Mice treated with allopregnanolone lived average of 112 days; mice treated with T0901317 lived to an average of 80 days, and mice treated with allopregnanolone plus T0907 lived to an average of 136 days.

Locomotor skills: Untreated NP-C mice begin to lose locomotor function beginning at 35 days of age, and continue this loss of function for the next 3-4 weeks of life. Mice treated with allopregnanolone or allopregnanolone plus T0901317 begin to lose motor function at 49 days; NP-C mice treated with T0901317 began to lose motor function at 42 days. In mice treated with T0901317 plus allopregnanolone, the loss of motor function is also more gradual, than with either allopregnanolone or with T0901317 alone. The results of these experiments are shown in FIG. 8.

Thus it is now established that a combination of therapies, neurosteroid and cholesterol-derived oxysterol therapy, affect the neurologic outcome and lifespan in NP-C mice, demonstrating that neurosteroids such as allopregnanolone, together with a LXR ligand provide a useful combination therapy for treating NP-C. Other brain diseases, including, but not limited to, congenital storage diseases, benefit from similar combination therapies.

While this invention has been disclosed with reference to specific embodiments, it is apparent that other embodiments and variations of this invention may be devised by others skilled in the art without departing from the true spirit and scope of the invention.

What is claimed is:

1. A method of providing therapy for a nervous system condition, wherein said nervous system condition is selected from a group consisting of Sandhoff, and Sanfilippo, said method comprising:
   administering to a patient in need thereof, a therapeutically effective amount of allopregnanolone formulation.

2. The method according to claim 1, wherein said pharmaceutical formulation is an oral formulation.

3. The method according to claim 1, wherein said therapeutically effective amount is administered in single or divided daily doses.

* * * * *